(12) United States Patent
Beckman et al.

(10) Patent No.: US 11,931,124 B2
(45) Date of Patent: Mar. 19, 2024

(54) SEGMENTED SHAFT FOR ROBOTIC SURGICAL TOOLS

(71) Applicant: Cilag GmbH International, Zug (CH)

(72) Inventors: Andrew T. Beckman, Cincinnati, OH (US); Charles J. Scheib, Loveland, OH (US); Jason A. Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 754 days.

(21) Appl. No.: 16/931,577

(22) Filed: Jul. 17, 2020

(65) Prior Publication Data

US 2022/0015845 A1    Jan. 20, 2022

(51) Int. Cl.
| | |
|---|---|
| *A61B 17/072* | (2006.01) |
| *A61B 34/00* | (2016.01) |
| *A61B 34/37* | (2016.01) |
| *B25J 5/00* | (2006.01) |
| *B25J 5/02* | (2006.01) |
| *B25J 15/02* | (2006.01) |
| *A61B 17/00* | (2006.01) |
| *A61B 17/29* | (2006.01) |
| *A61B 34/30* | (2016.01) |

(52) U.S. Cl.
CPC .............. *A61B 34/37* (2016.02); *A61B 34/74* (2016.02); *B25J 5/007* (2013.01); *B25J 5/02* (2013.01); *B25J 15/026* (2013.01); *A61B 2017/00473* (2013.01); *A61B 2017/00477* (2013.01); *A61B 2017/07285* (2013.01); *A61B 2017/2943* (2013.01); *A61B 2034/301* (2016.02); *A61B 2034/302* (2016.02); *A61B 2034/305* (2016.02)

(58) Field of Classification Search
CPC ........... A61B 2017/00473; A61B 2017/00477; A61B 2017/07285; A61B 17/072
See application file for complete search history.

(56) References Cited

U.S. PATENT DOCUMENTS

| | | | |
|---|---|---|---|
| 9,861,366 B2 * | 1/2018 | Aranyi | ................. A61B 17/068 |
| 10,363,037 B2 * | 7/2019 | Aronhalt | .............. A61B 17/072 |
| (Continued) | | | |

FOREIGN PATENT DOCUMENTS

| | | |
|---|---|---|
| CN | 111358561 A | 7/2020 |
| WO | 2019135940 A1 | 11/2019 |

OTHER PUBLICATIONS

Written Report and International Search Report from PCT Application No. PCT/IB2021/056394 dated Oct. 11, 2021.

*Primary Examiner* — Gloria R Weeks
(74) *Attorney, Agent, or Firm* — Vorys, Sater, Seymour and Pease, LLP

(57) ABSTRACT

A robotic surgical tool includes a drive housing having a lead screw extending from a first end of the drive housing, a carriage movably mounted to the lead screw at a carriage nut secured to the carriage, and an elongate shaft extending from the carriage and penetrating the first end, the shaft having an end effector arranged at a distal end thereof and comprising a proximal shaft portion releasably coupled to a distal shaft portion at a releasable interface. Proximal and distal portions of one or more mechanisms of the surgical tool extend from the carriage to the end effector within the proximal and distal shaft portions, respectively, and the one or more mechanisms are operable to operate or articulate the end effector.

14 Claims, 27 Drawing Sheets

(56) References Cited

U.S. PATENT DOCUMENTS

| | | | | |
|---|---|---|---|---|
| 11,039,835 B2* | 6/2021 | Wixey | ............... | F16H 25/2472 |
| 11,678,870 B2* | 6/2023 | Beckman | ......... | A61B 17/07207 606/1 |
| 11,701,117 B2* | 7/2023 | Beckman | .............. | A61G 13/10 227/175.3 |
| 11,751,960 B2* | 9/2023 | Beckman | ........... | A61B 1/00133 606/130 |
| 2005/0021018 A1* | 1/2005 | Anderson | .............. | A61B 34/70 606/28 |
| 2007/0023477 A1* | 2/2007 | Whitman | ............. | A61B 17/068 227/175.1 |
| 2010/0320252 A1* | 12/2010 | Viola | ................... | A61B 17/068 227/176.1 |
| 2013/0296886 A1* | 11/2013 | Green | .................... | A61B 34/70 606/130 |
| 2014/0276761 A1 | 9/2014 | Parihar et al. | | |
| 2014/0352463 A1* | 12/2014 | Parihar | ............ | A61B 17/07207 74/25 |
| 2015/0073339 A1* | 3/2015 | Pacheco | ............ | A61M 25/0113 604/95.01 |
| 2015/0080924 A1* | 3/2015 | Stulen | ............ | A61B 17/320092 606/169 |
| 2019/0008600 A1 | 1/2019 | Pedros et al. | | |
| 2021/0015572 A1* | 1/2021 | Gomez | ................ | A61B 34/35 |
| 2021/0022815 A1 | 1/2021 | Abbott | | |
| 2022/0096084 A1* | 3/2022 | Beckman | ............... | A61B 34/76 |

\* cited by examiner

SEGMENTED SHAFT FOR ROBOTIC SURGICAL TOOLS

TECHNICAL FIELD

The systems and methods disclosed herein are directed to robotic surgical tools and, more particularly to, a segmented shaft for a robotic surgical tool.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms manipulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a drive housing having a lead screw extending from a first end of the drive housing, a carriage movably mounted to the lead screw at a carriage nut secured to the carriage, an elongate shaft extending from the carriage and penetrating the first end, the shaft having an end effector arranged at a distal end thereof and comprising a proximal shaft portion releasably coupled to a distal shaft portion at a releasable interface, and proximal and distal portions of one or more mechanisms of the surgical tool extending from the carriage to the end effector within the proximal and distal shaft portions, respectively, wherein the one or more mechanisms are operable to operate or articulate the end effector, and wherein the proximal and distal portions are releasably coupled at the releasable interface. In a further embodiment, the robotic surgical tool further includes a drive input arranged at the first end and operatively coupled to the lead screw such that rotation of the drive input correspondingly rotates the lead screw, and an instrument driver arranged at an end of a robotic arm and matable with the drive housing at the first end, the instrument driver providing a drive output matable with the drive input such that rotation of the drive output correspondingly rotates the drive input and thereby rotates the lead screw, wherein rotation of the lead screw moves the carriage and the carriage nut axially along the lead screw and thereby moves the one or more mechanisms and the end effector distally or proximally. In another further embodiment, the shaft penetrates the instrument driver by extending through a central aperture defined longitudinally through the instrument driver. In another further embodiment, the robotic surgical tool further includes a latch mechanism that rotationally fixes the distal shaft portion to the proximal shaft portion when engaged and thereby prevents the proximal and distal shaft portions from separating. In another further embodiment, the robotic surgical tool further includes an activating mechanism mounted to the carriage and actuatable to advance or retract the proximal and distal shaft portions relative to the one or more mechanisms and thereby close or open jaws of the end effector. In another further embodiment, the releasable interface includes a proximal channel retainer at least partially receivable within the proximal shaft portion, and one or more internal couplings supported by the proximal channel retainer, each internal coupling releasably coupling the proximal and distal portions of a corresponding one of the one or more mechanisms. In another further embodiment, the one or more internal couplings comprises an inner grounding shaft coupling comprising a proximal inner grounding shaft extending within the proximal shaft portion from the carriage, a distal inner grounding shaft extending within the distal shaft portion from the end effector, one or more projections provided by the proximal inner grounding shaft, and one or more pockets defined on the distal inner grounding shaft and configured to receive and axially retain the one or more projections and thereby couple the proximal and distal inner grounding shafts. In another further embodiment, the one or more internal couplings further comprises a drive member coupling comprising proximal drive member portions corresponding to first and second drive members extending from the carriage and extending within corresponding slots defined in the proximal inner grounding shaft, distal drive member portions corresponding to the first and second drive members extending from the end effector and extending within corresponding slots defined in the distal inner grounding shaft, first matable features provided on the proximal drive member portions, and second matable features provided on the distal drive member portions and matable with the first matable features to interconnect the proximal and distal drive members, wherein actuation of the first and second drive members moves the proximal and distal drive member portions and thereby articulates the end effector. In another further embodiment, the one or more internal couplings comprises a closure tube coupling that releasably couples the proximal and distal shaft portions, the closure tube coupling comprising a proximal tube coupling secured to the proximal shaft portion, and a distal tube coupling secured to the distal shaft portion and matable with the proximal tube coupling. In another further embodiment, the proximal and distal tube couplings comprise matable bayonet-style couplings. In another further embodiment, the one or more internal couplings comprises a firing rod coupling comprising a proximal firing rod portion corresponding to a firing rod extending from the carriage and providing a first matable feature, and a distal firing rod portion corresponding to the firing rod extending from the end effector and providing a second matable feature matable with the first matable feature to interconnect the proximal and distal firing rod portions, wherein actuation of the firing rod causes the proximal and distal firing rod portions to advance or retract and simultaneously advance or retract a knife at the end effector. In another further embodiment, the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

Embodiments disclosed herein may further include a method of disassembling a surgical tool that includes rotating a distal shaft portion in a first angular direction relative to a proximal shaft portion, the distal and proximal shaft portions forming part of the surgical tool that includes a drive housing having a lead screw extending from a first end of the drive housing, a carriage movably mounted to the lead screw at a carriage nut secured to the carriage, an elongate shaft extending from the carriage and penetrating the first end, the shaft comprising the proximal and distal shaft portions releasably coupled at a releasable interface, an end effector arranged at a distal end of the distal shaft portion, and proximal and distal portions of one or more mechanisms of the surgical tool extending from the carriage to the end effector within the proximal and distal shaft portions, respectively. The method may further include disengaging the proximal and distal portions as the distal shaft rotates in the first angular direction, the one or more mechanisms being operable to operate or articulate the end effector, and axially separating the distal shaft portion from the proximal shaft portion at the releasable interface. In a further embodiment, rotating the distal shaft portion relative to the proximal shaft portion is preceded by rotationally fixing the distal shaft portion to the proximal shaft portion with a latch mechanism, and disengaging the latch mechanism to allow the distal shaft portion to rotate relative to the proximal shaft portion. In another further embodiment, the method further includes disengaging one or more internal couplings as the distal shaft rotates in the first angular direction, wherein each internal coupling releasably couples the proximal and distal portions of a corresponding one of the one or more mechanisms of the surgical tool. In another further embodiment, the one or more internal couplings comprises a drive member coupling comprising proximal drive member portions corresponding to first and second drive members extending from the carriage, and distal drive member portions corresponding to the first and second drive members extending from the end effector, the method further comprising disengaging first matable features provided on the proximal drive member portions from second matable features provided on the distal drive member portions and thereby disconnecting the proximal and distal drive members. In another further embodiment, the one or more internal couplings comprises a closure tube coupling that releasably couples the proximal and distal shaft portions and comprises a proximal tube coupling secured to the proximal shaft portion, and a distal tube coupling secured to the distal shaft portion and matable with the proximal tube coupling, the method further comprising actuating an activating mechanism mounted to the carriage and thereby advancing or retracting the proximal and distal shaft portions, closing or opening jaws of the end effector as the proximal and distal shaft portions move relative to the one or more mechanisms, and disengaging the proximal and distal tube couplings as the distal shaft rotates in the first angular direction. In another further embodiment, the one or more internal couplings comprises a firing rod coupling comprising a proximal firing rod portion corresponding to a firing rod extending from the carriage, and a distal firing rod portion corresponding to the firing rod extending from the end effector, the method further comprising disengaging a first matable feature provided on the proximal firing rod portion from a second matable feature provided on the distal firing rod portion as the distal shaft rotates in the first angular direction and thereby disconnecting the proximal and distal firing rod portions.

Embodiments disclosed herein may further provide another robotic surgical tool that includes a drive housing having a lead screw extending from a first end of the drive housing, a carriage movably mounted to the lead screw at a carriage nut secured to the carriage, an elongate shaft extending from the carriage and penetrating the first end, the shaft having an end effector arranged at a distal end thereof and comprising a proximal shaft portion releasably coupled to a distal shaft portion at a releasable interface, and a firing rod extending from the carriage and operatively coupled to a knife at the end effector, the firing rod comprising a proximal firing rod portion releasably coupled to a distal firing rod portion at the releasable interface, wherein longitudinal movement of the firing rod correspondingly moves the knife in the same direction relative to the proximal and distal shaft portions and simultaneously closes or opens jaws of the end effector. In a further embodiment, the robotic surgical tool further includes a first matable feature provided on the proximal firing rod portion, and a second matable feature provided on the distal firing rod portion and matable with the first matable feature to interconnect the proximal and distal firing rod portions.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
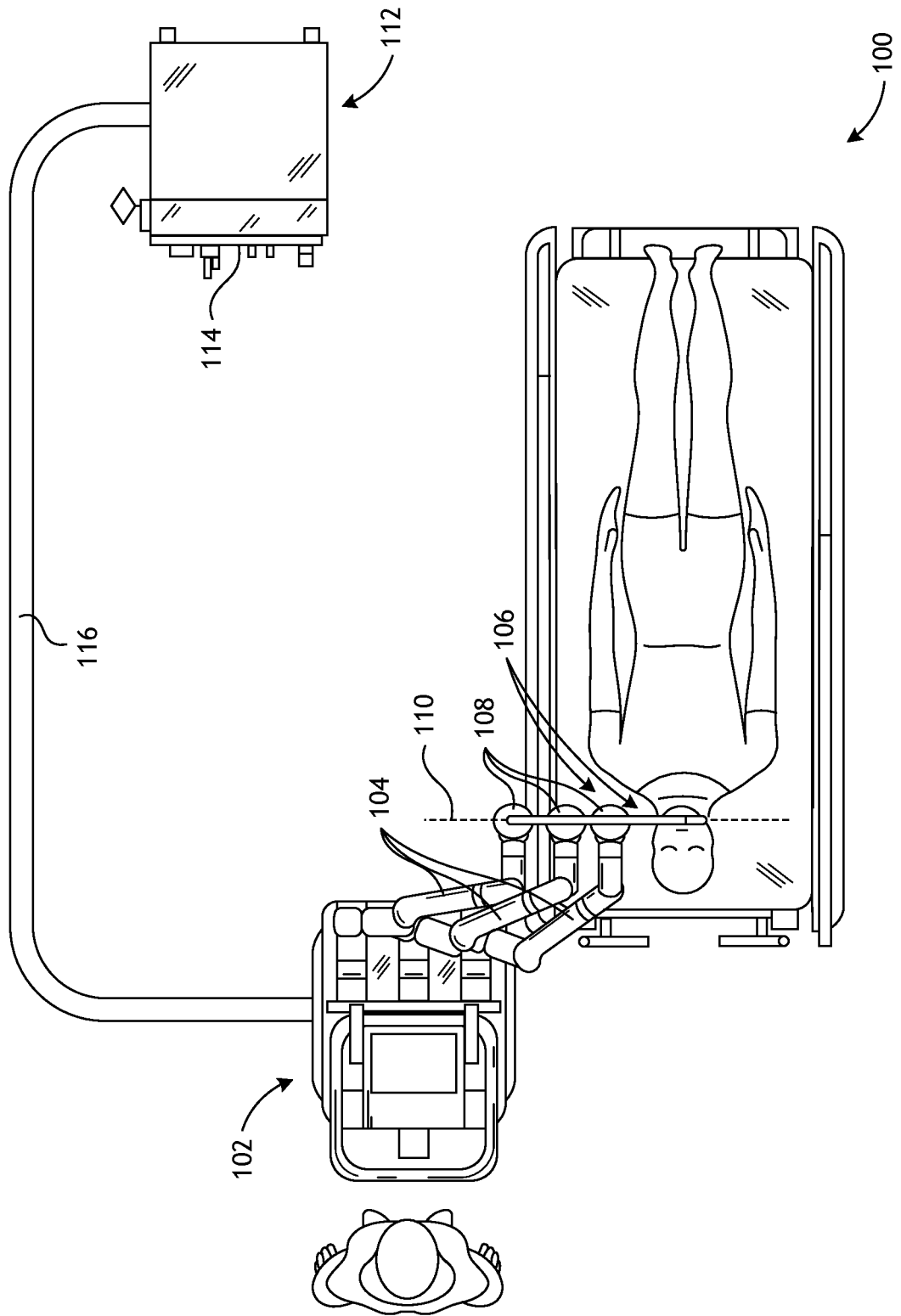
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
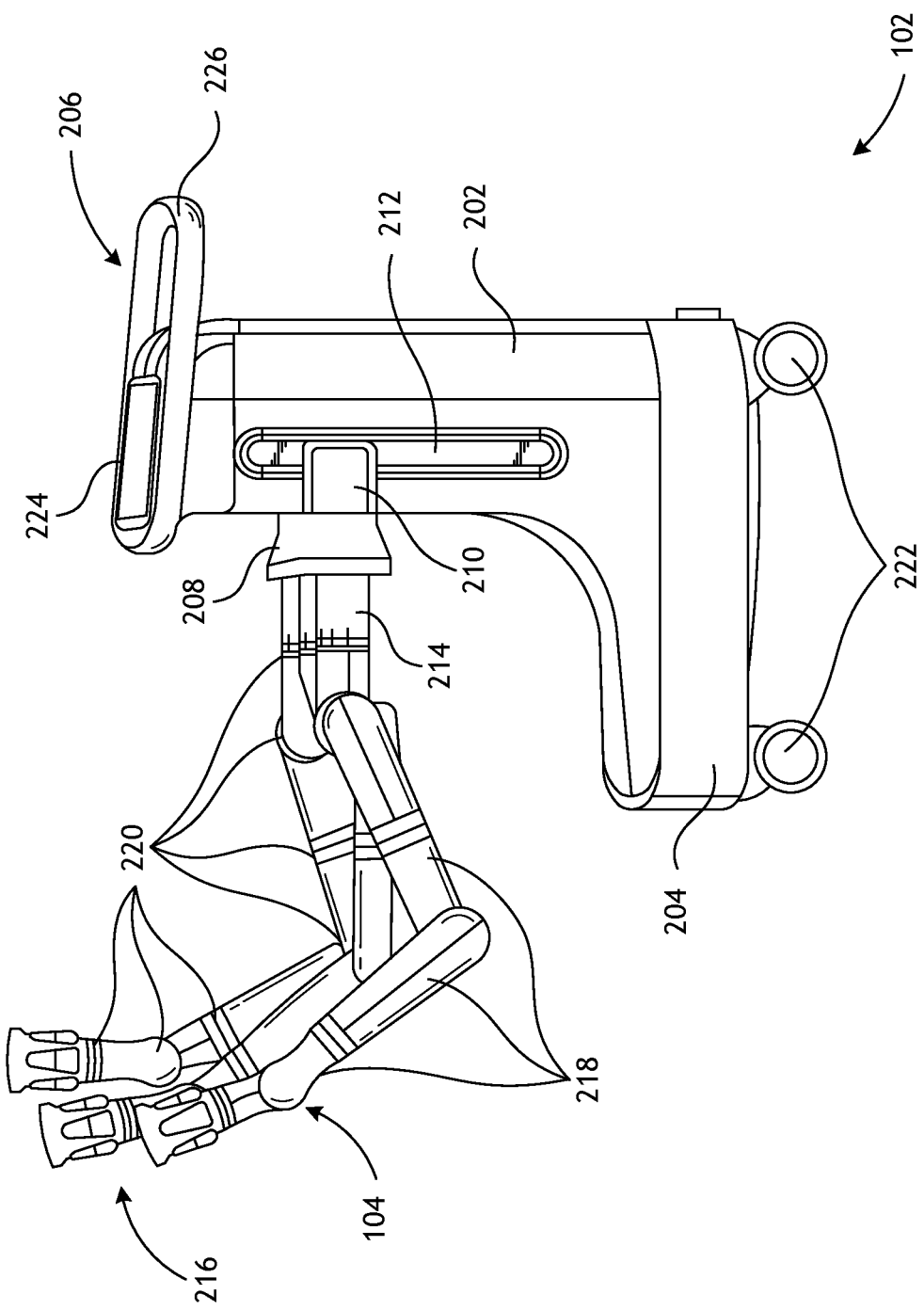
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
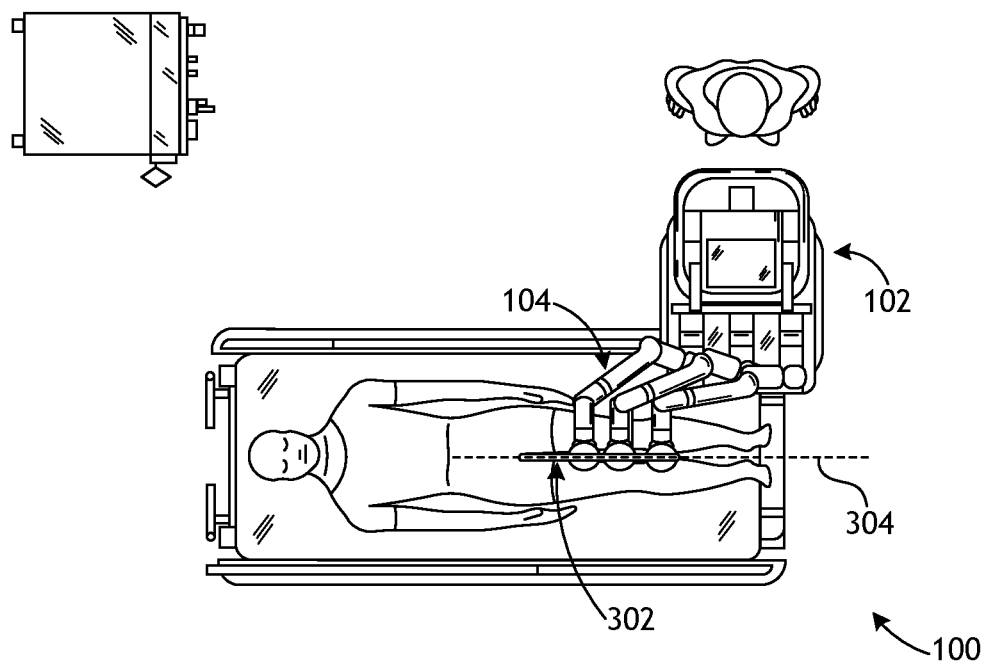
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
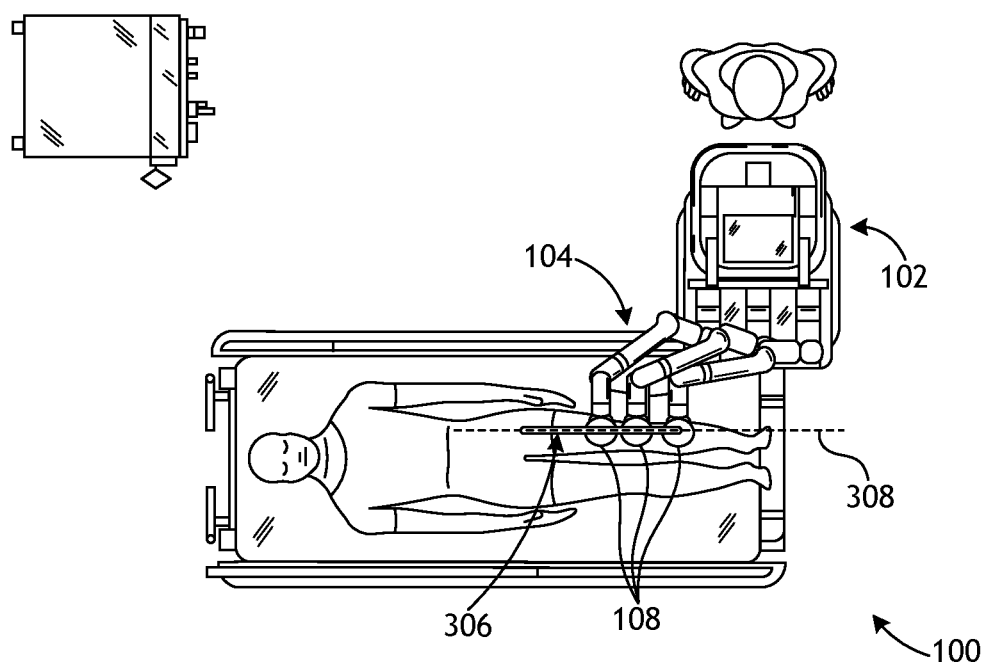
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
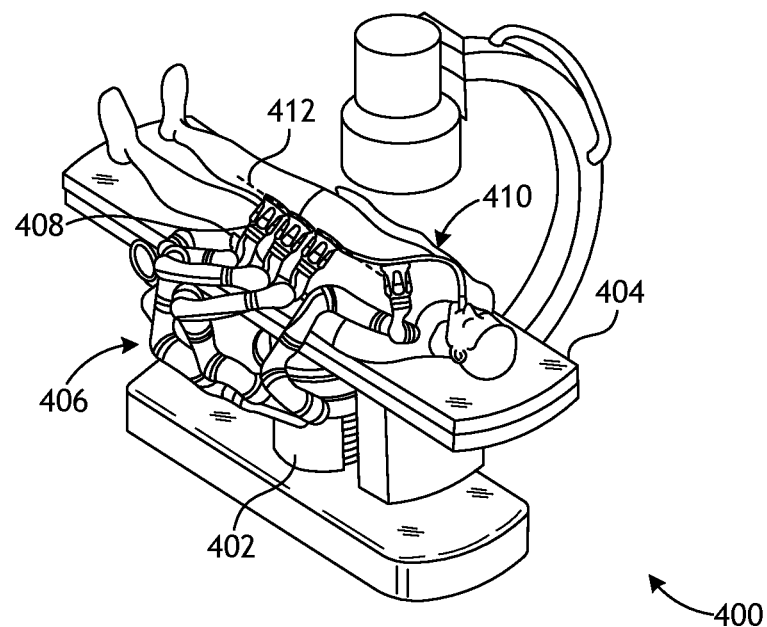
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
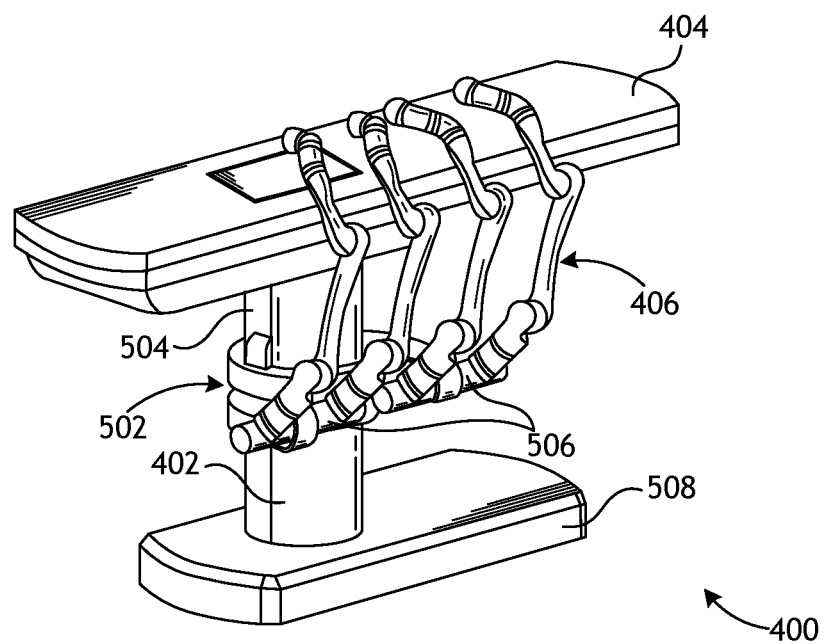
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
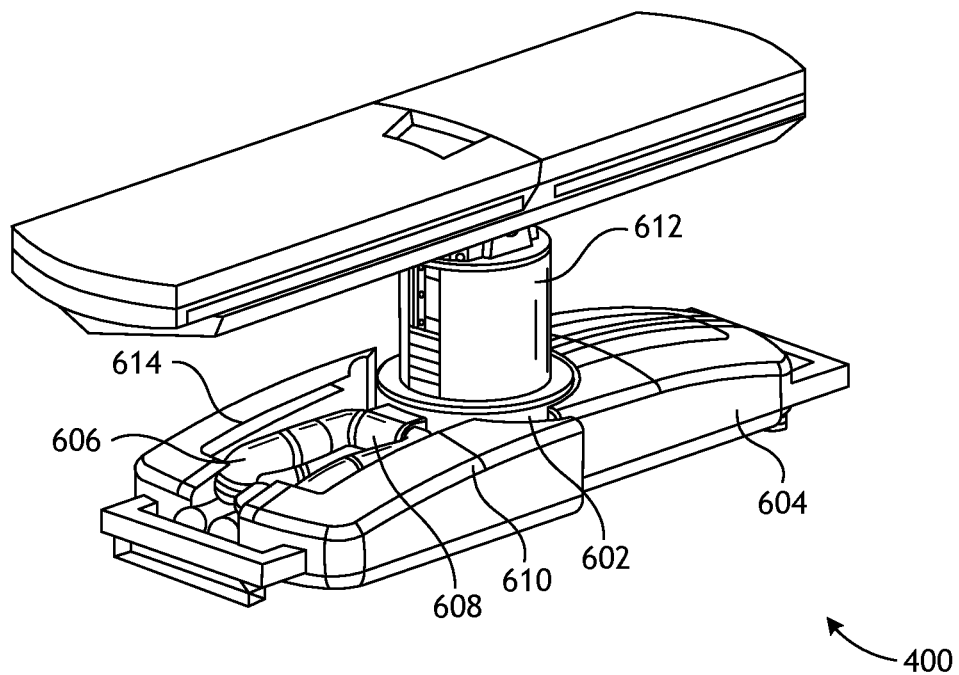
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
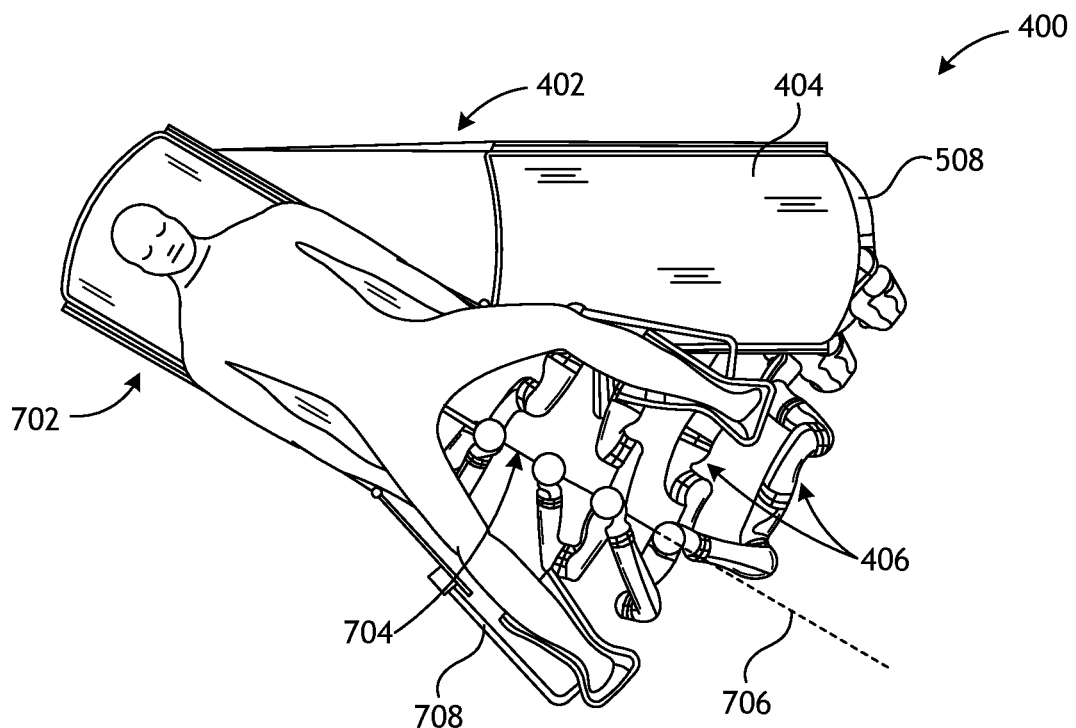
FIG. 7A illustrates an embodiment of a table-based robotic system configured for a ureteroscopy procedure.
Figure 7B:
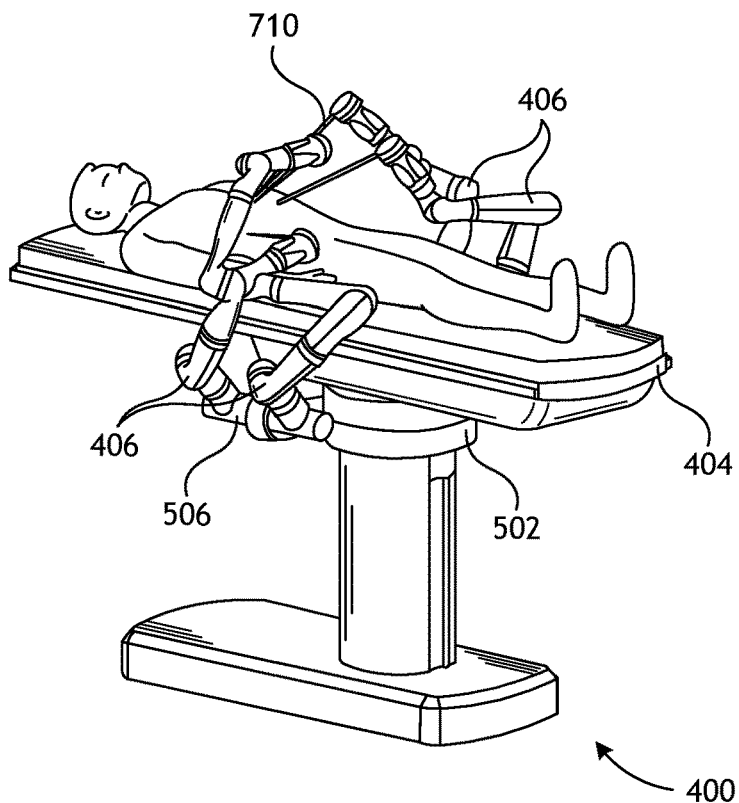
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
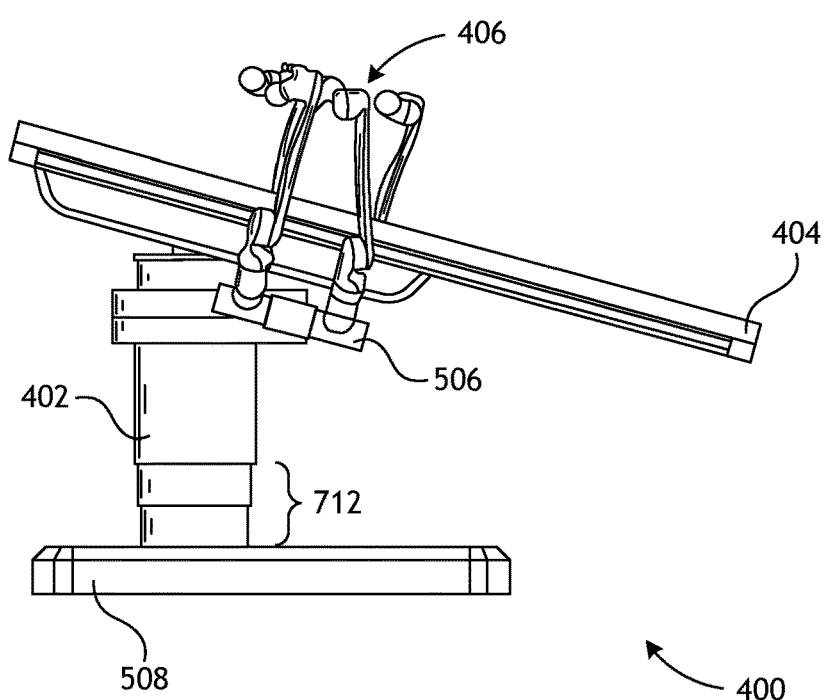
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
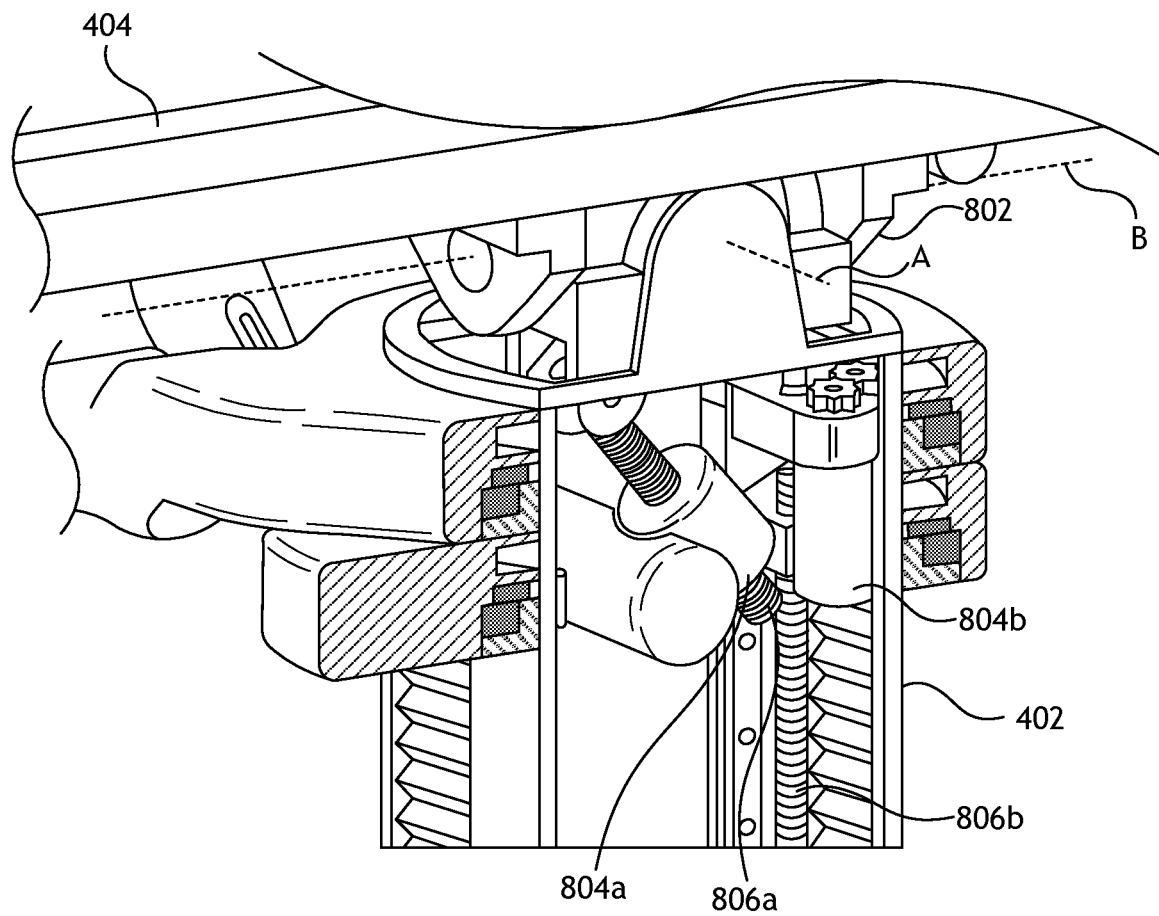
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
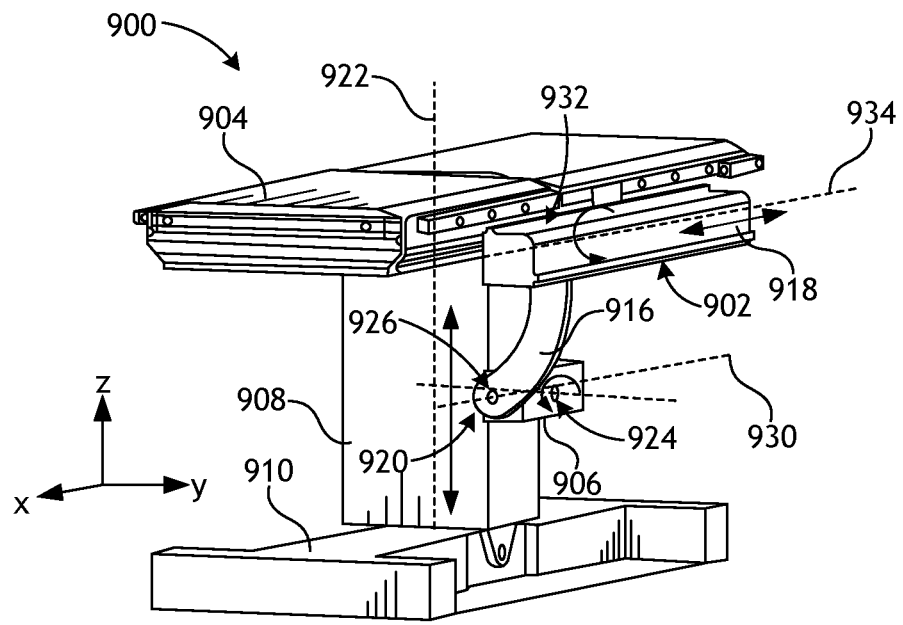
FIG. 9A illustrates an alternative embodiment of a table-based robotic system.
Figure 9B:
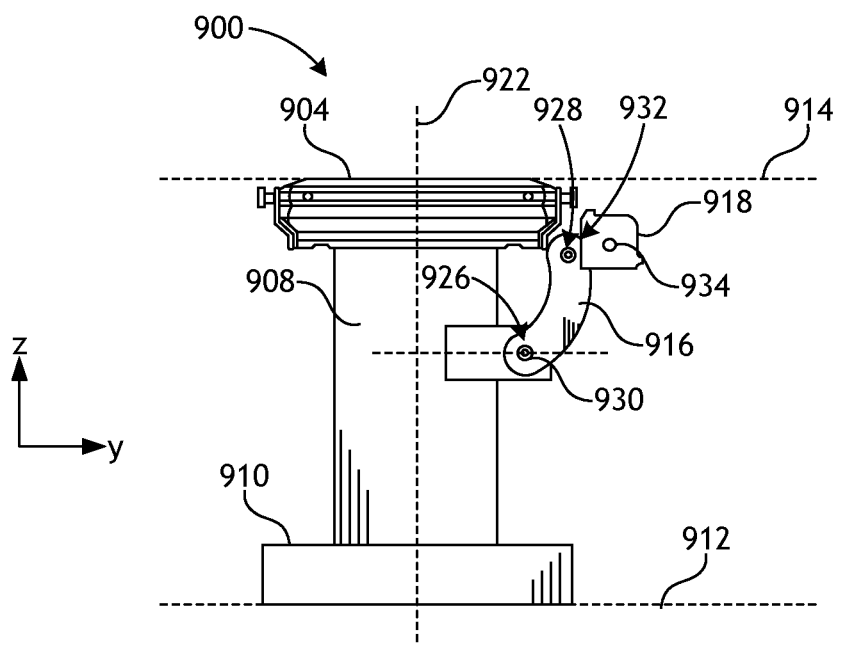
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
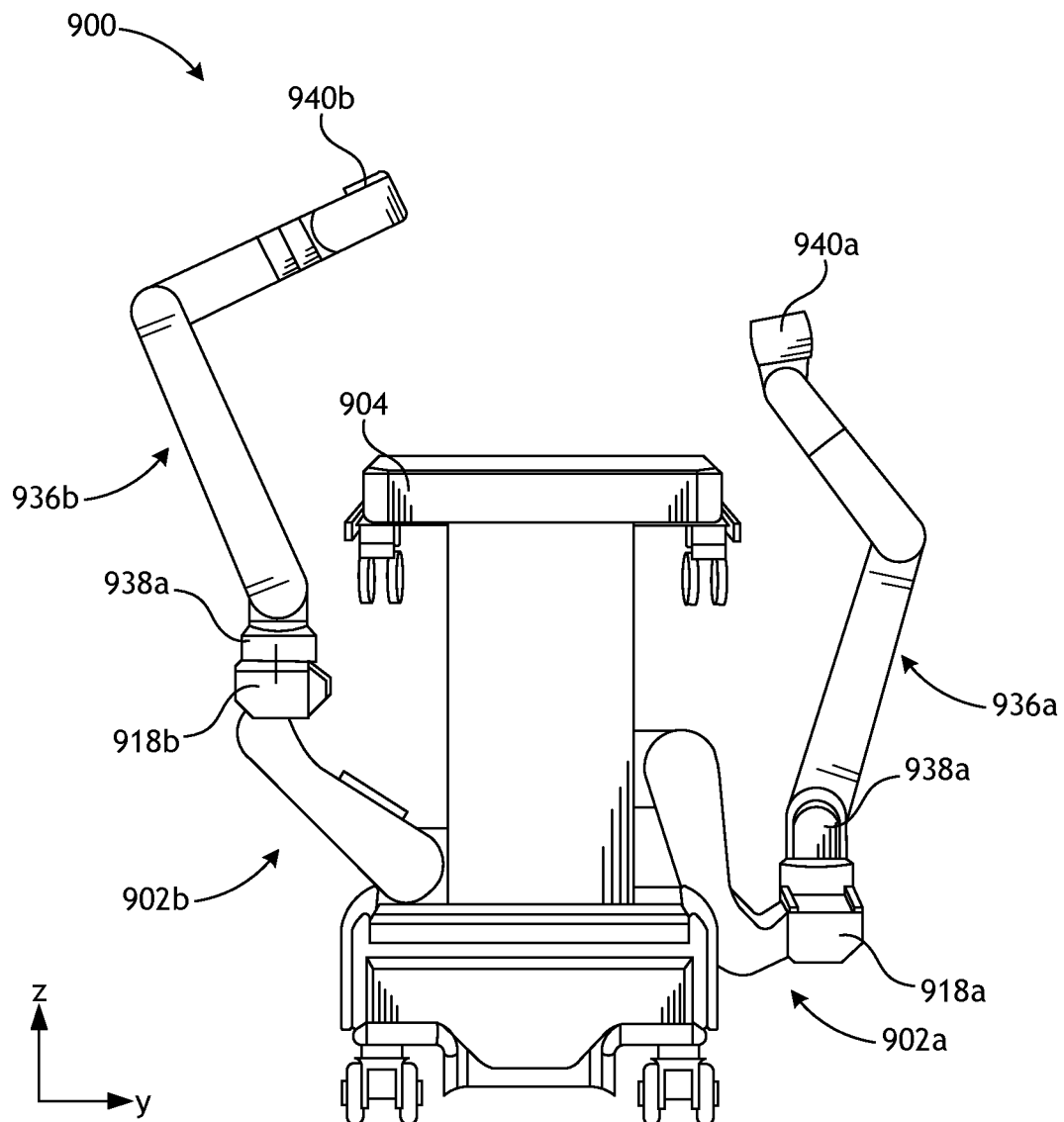
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
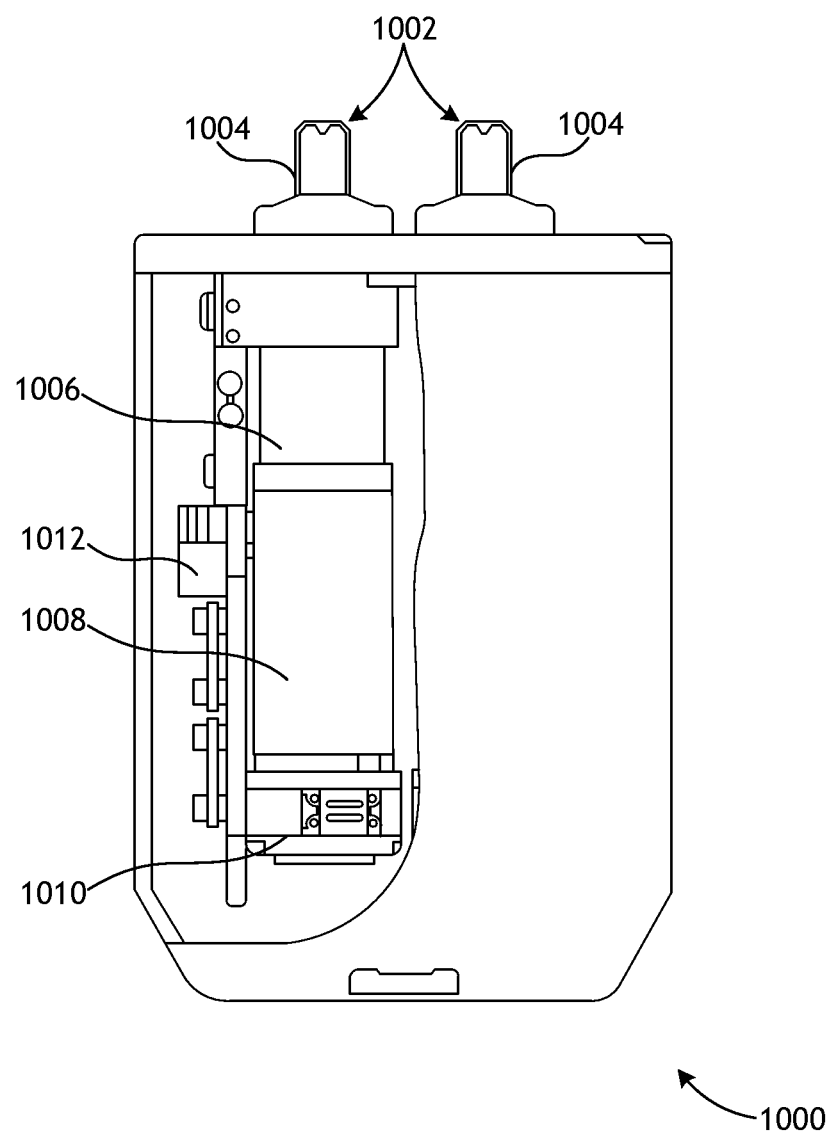
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
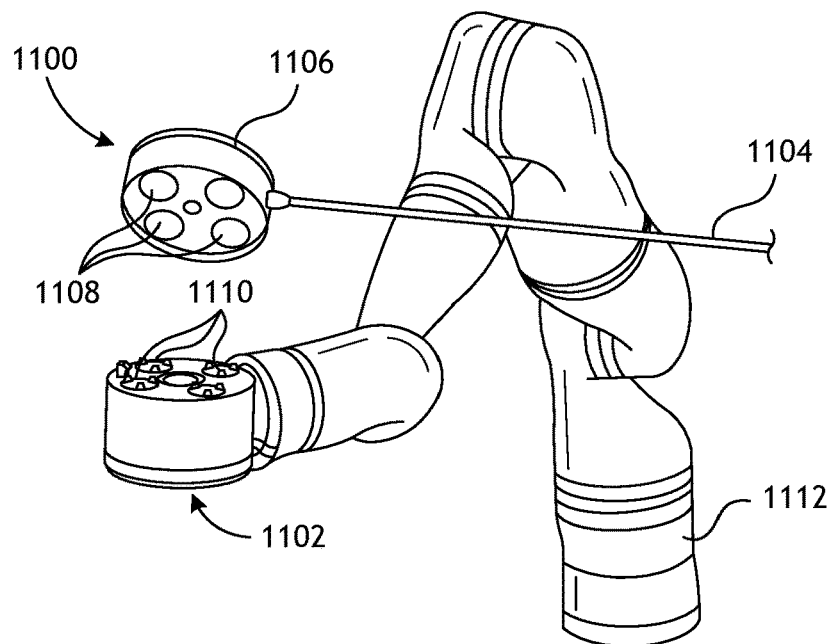
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
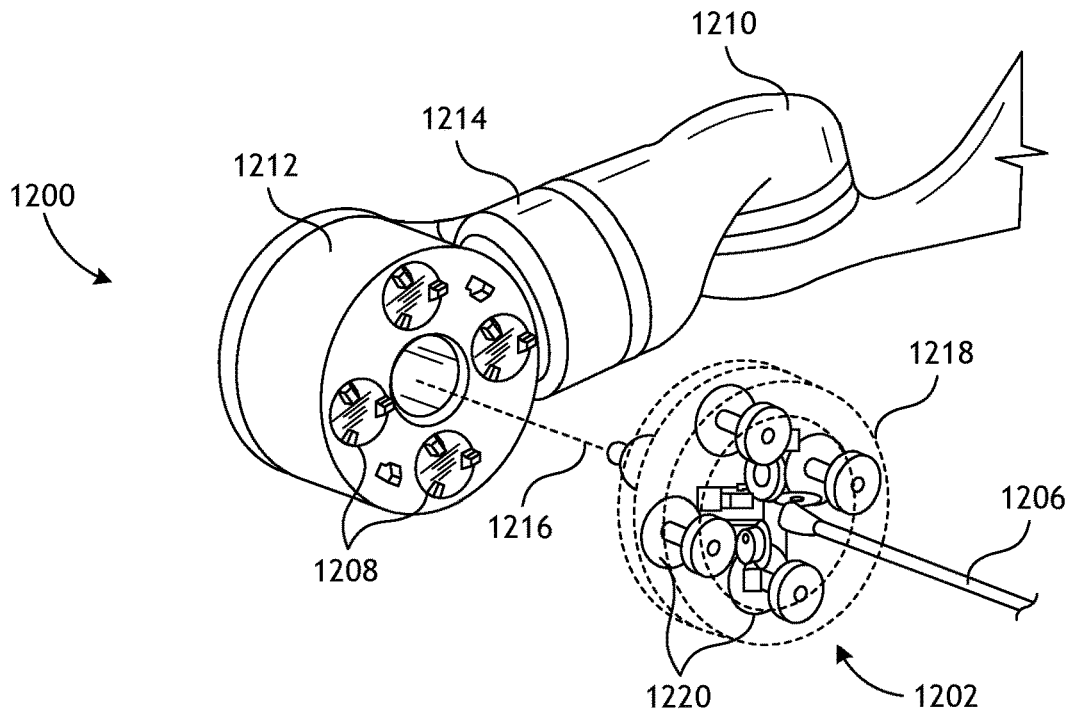
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation.

Accordingly, the parallelism of the axes of the drive outputs 1208, the drive inputs 1220, and the instrument shaft 1206 allows for the shaft rotation without tangling any control tendons.

Figure 13:
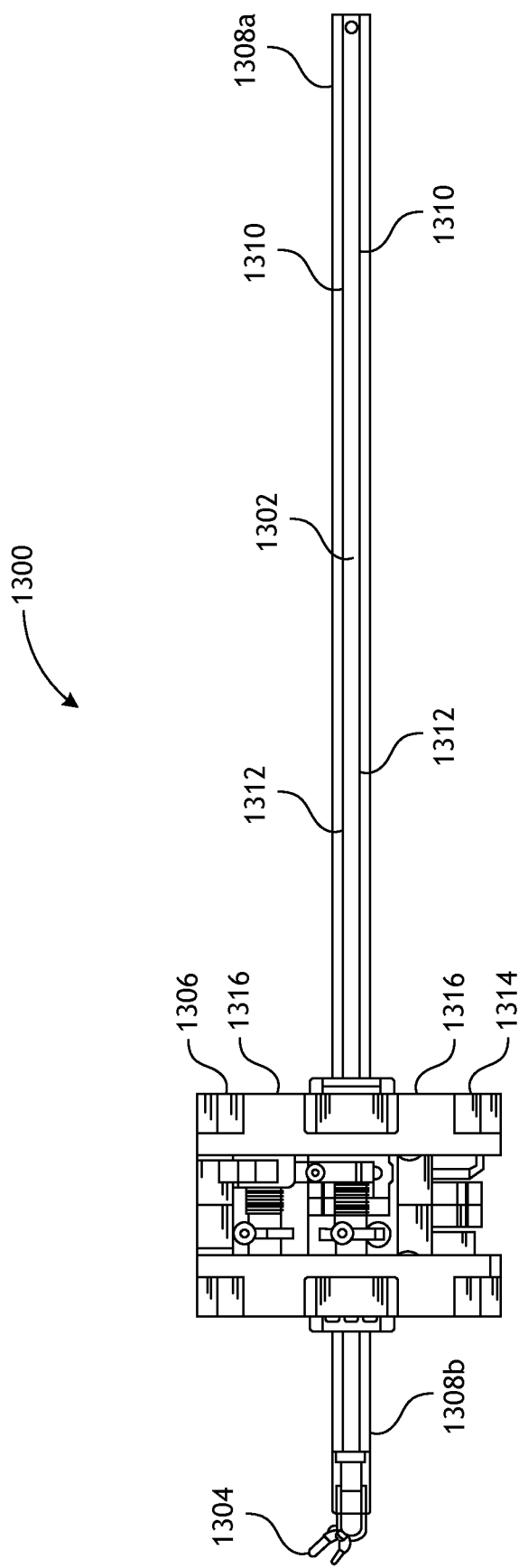
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308*a* and a distal portion 1308*b*. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
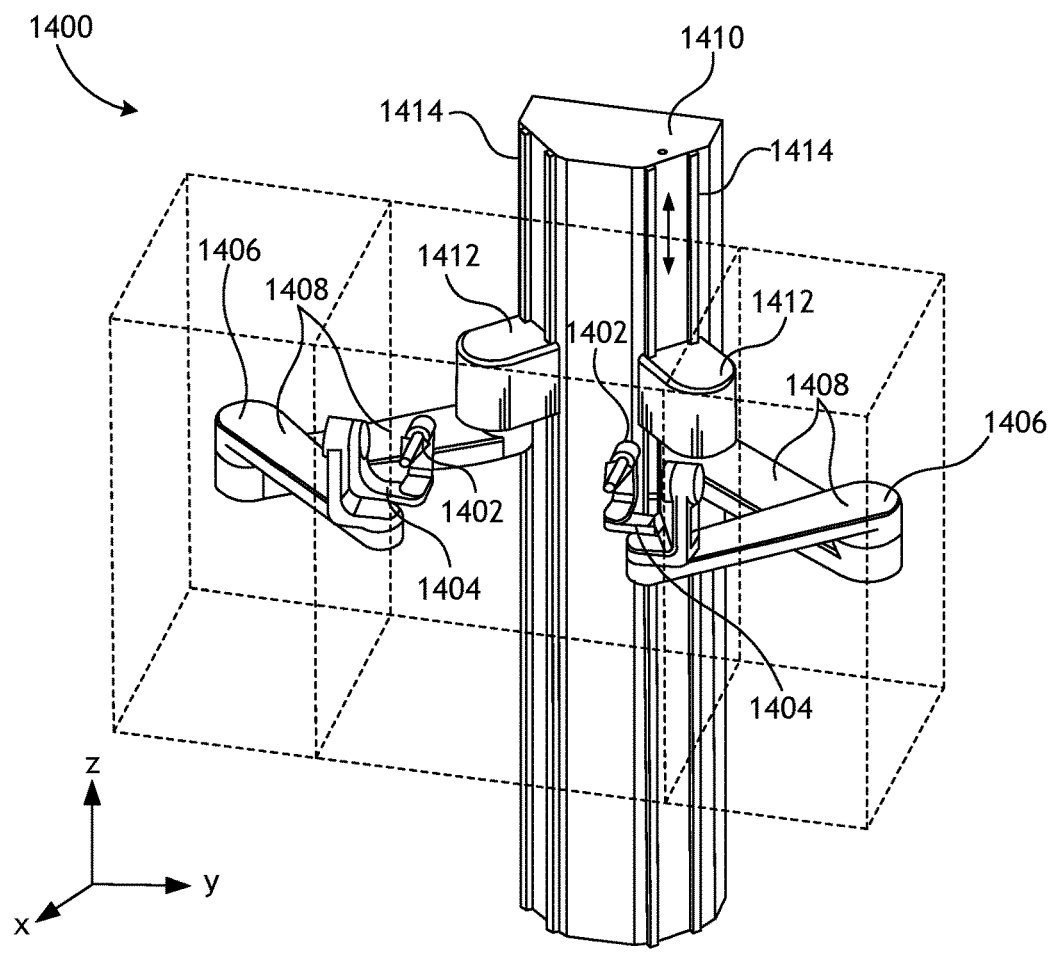
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
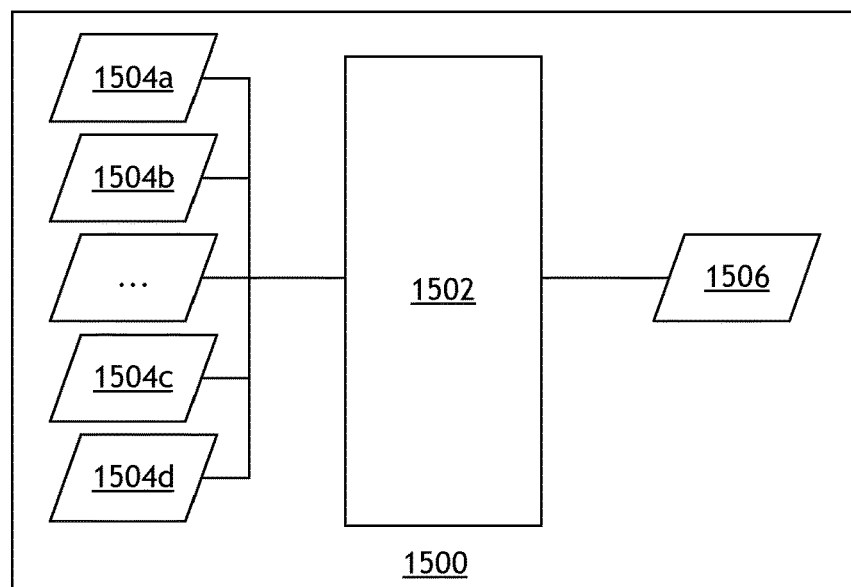
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504*a*, 1504*b*, 1504*c*, and 1504*d* to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504*a*-*d* are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction

Embodiments of the disclosure relate to surgical tools having a shaft that may be modular and otherwise segmented into at least two portions or sections that are releasably coupled. A releasable interface between the sections of the shaft may include a latch mechanism that may be manually manipulated by a user (e.g., a doctor, a nurse, an operator, etc.) to help facilitate the process of separating the distal and proximal shaft portions. The releasable interface may prove advantageous in converting an end effector disposed at the end of the distal shaft portion into a disposable or consumable component part of the surgical tool. The releasable interface allows distal portions of the surgical tool to be removed and replaced with a new or refurbished end effector. This may allow operators to easily and quickly replace worn, used, or depleted end effector components (e.g., knives, clip cartridges, etc.). This also allows the operator to easily and quickly replace the end effector with an end effector having a different length, or an end effector with differently designed jaws.

3. Description

Figure 16:
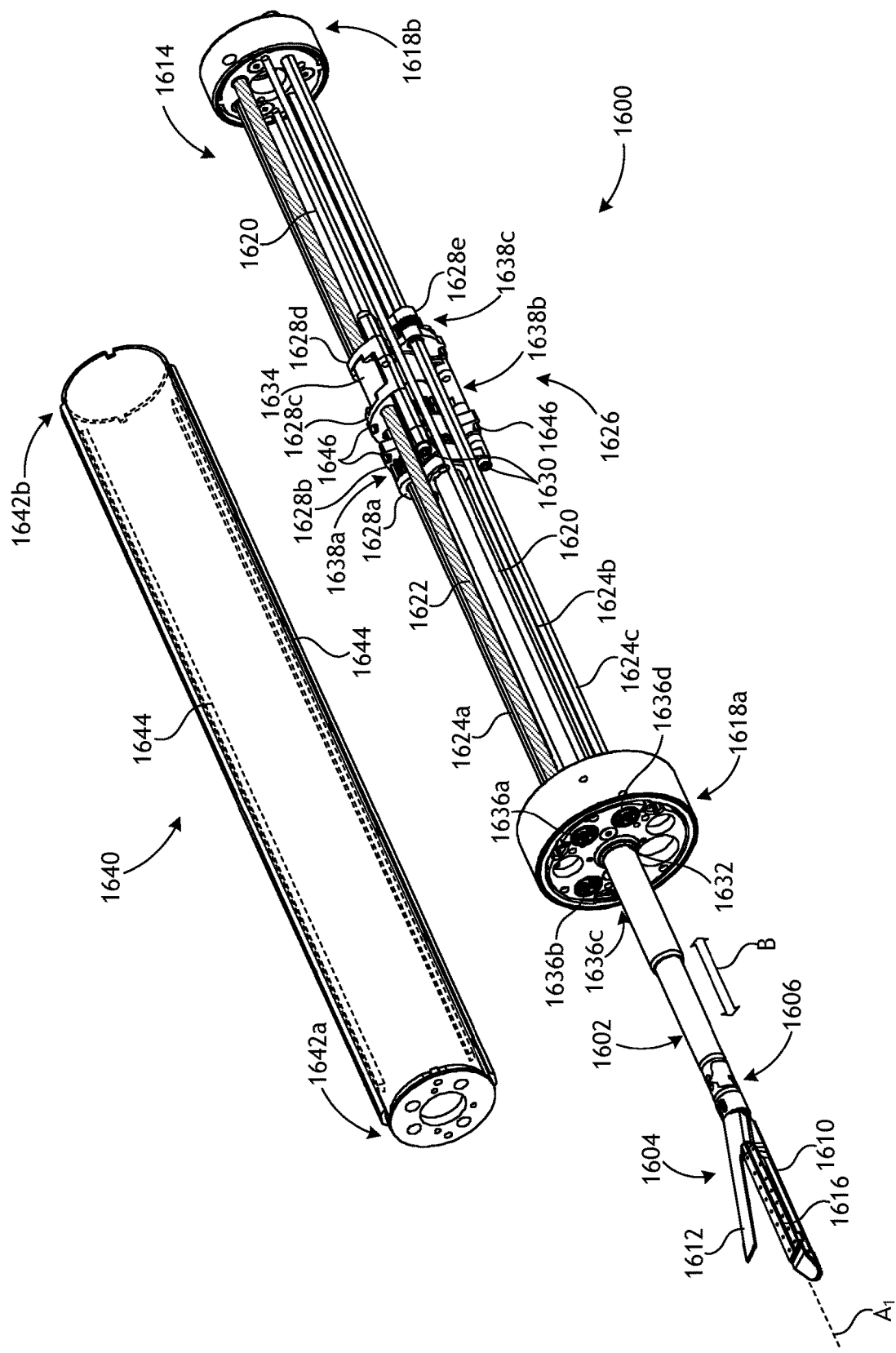
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments having opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 is referred to as a "cartridge" or "channel" jaw, and the second jaw 1612 is referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing 1614 that houses an actuation system designed to facilitate articulation of the wrist 1606 and actuation (operation) of the end effector 1604 (e.g., clamping, firing, rotation, articulation, energy delivery, etc.). The drive housing 1614, alternately referred to as a "stage," provides various coupling features that releasably couple the surgical tool 1600 to an instrument driver of a robotic surgical system, as described in more detail below.

The drive housing 1614 includes a plurality of drive members (obscured in FIG. 16), such as cables, bands, lines, cords, wires, ropes, strings, twisted strings, or elongate members, which extend to the wrist 1606 and the end effector 1604. Selective actuation of one or more of the drive members causes the end effector 1604 to articulate (pivot) relative to the shaft 1602 at the wrist 1606. Selective actuation of one or more other drive members causes the end effector 1604 to actuate (operate). Actuating the end effector 1604 may include closing and/or opening the jaws, 1610, 1612, and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot 1616 defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the drive housing 1614 has a first or "distal" end 1618a and a second or "proximal" end 1618b opposite the first end 1618a. The first end 1618a is alternately referred to as a "handle" because it is typically gripped by a user when attaching the surgical tool to an instrument driver. In some embodiments, one or more struts 1620 (two shown) extend longitudinally between the first and second ends 1618a,b to help fix the distance between the first and second ends 1618a,b, provide structural stability to the drive housing 1614, and secure the first end 1618a to the second end 1618b. In other embodiments, however, the struts 1620 may be omitted, without departing from the scope of the disclosure.

The drive housing 1614 may also include a lead screw 1622 and one or more splines 1624, which also extend longitudinally between the first and second ends 1618a,b. In the illustrated embodiment, the drive housing 1614 includes a first spline 1624a, a second spline 1624b, and a third spline 1624c. While three splines 1624a-c are depicted in the drive housing 1614, more or less than three may be included in the surgical tool 1600. Unlike the struts 1620, the lead screw 1622 and the splines 1624a-c are rotatably mounted to the first and second ends 1618a,b. As discussed herein, selective rotation (actuation) of the lead screw 1622 and the splines 1624a-c causes various functions of the drive housing 1614 to transpire, such as translating the end effector 1604 along the longitudinal axis $A_1$ (e.g., z-axis translation) causing the end effector 1604 to articulate (pivot) at the wrist 1606, causing the jaws 1610, 1612 to open and close, and causing the end effector 1604 to fire (operate).

The drive housing 1614 further includes a carriage 1626 movably mounted along the lead screw 1622 and the splines 1624a-c, and housing various activating mechanisms configured to cause operation of specific functions of the end effector 1604. The carriage 1626 may comprise two or more layers, shown in FIG. 16 as a first layer 1628a, a second layer 1628b, a third layer 1628c, a fourth layer 1628d, and a fifth layer 1628e. The lead screw 1622 and the splines 1624a-c each extend through portions of one or more of the layers 1628a-e to allow the carriage 1626 to translate along the longitudinal axis $A_1$ with respect to (relative to) the lead screw 1622 and the splines 1624a-c. In some embodiments, the layers 1628a-e may be secured to each other in series using one or more mechanical fasteners 1630 (two visible) extending between the first layer 1628a and the fifth layer 1628e and through coaxially aligned holes defined in some or all of the layers 1628a-e. While five layers 1628a-e are depicted, the carriage 1626 can include more or less than five, without departing from the scope of the disclosure.

The shaft 1602 is coupled to and extends distally from the carriage 1626 through the first end 1618a of the drive housing 1614. In the illustrated embodiment, for example, the shaft 1602 penetrates the first end 1618a at a central aperture 1632 defined through the first end 1618a. The carriage 1626 is movable between the first and second ends 1618a,b along the longitudinal axis $A_1$ (e.g., z-axis translation) and is thereby able to advance or retract the end effector 1604 relative to the drive housing 1614, as indicated by the arrows B. More specifically, in some embodiments, the carriage 1626 includes a carriage nut 1634 mounted to the lead screw 1622 and secured between the third and fourth layers 1628c,d. The outer surface of the lead screw 1622 defines outer helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the drive housing 1614.

As indicated above, the lead screw 1622 and the splines 1624a-c are rotatably mounted to the first and second ends 1618a,b. More specifically, the first end 1618a of the drive housing 1614 may include one or more rotatable drive inputs actuatable to independently drive (rotate) the lead screw 1622 and the splines 1624a-c. In the illustrated embodiment, the drive housing 1614 includes a first drive input 1636a, a second drive input 1636b, a third drive input 1636c (occluded by the shaft 1602, see FIG. 17B), and a fourth drive input 1636d. As described below, each drive input 1636a-d may be matable with a corresponding drive output of an instrument driver such that movement (rotation) of a given drive output correspondingly moves (rotates) the associated drive input 1636a-d and thereby rotates the mated lead screw 1622 or spline 1624a-c. While only four drive inputs 1636a-d are depicted, more or less than four may be included in the drive housing 1614 as need requires.

The first drive input 1636a may be operatively coupled to the lead screw 1622 such that rotation (actuation) of the first drive input 1636a correspondingly rotates the lead screw 1622, which causes the carriage nut 1634 and the carriage 1626 to advance or retract along the longitudinal axis $A_1$, depending on the rotational direction of the lead screw 1622. As used herein the phrase "operatively coupled" refers to a coupled engagement, either directly or indirectly, where movement of one component causes corresponding movement of another component. With respect to the first drive input 1636a being operatively coupled to the lead screw 1622, such operative coupling may be facilitated through intermeshed gears (not shown) arranged within the second end 1618a, but could alternatively be facilitated through other mechanical means, such as cables, pulleys, drive rods, direct couplings, etc., without departing from the scope of the disclosure.

The second drive input 1636b may be operatively coupled to the first spline 1624a such that rotation (actuation) of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and thereby open or close the jaws 1610, 1612, depending on the rotational direction of the first spline 1624a.

The third drive input 1636c may be operatively coupled to the second spline 1624b such that rotation (actuation) of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and thereby cause the wrist 1606 to articulate in at least one degree of freedom, depending on the rotational direction of the second spline 1624b.

The fourth drive input 1636d may be operatively coupled to the third spline 1624c such that rotation (actuation) of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the cutting element (knife) at the end effector 1604. Accordingly, rotating the fourth drive input 1636d will correspondingly actuate the third activating mechanism 1638c and thereby cause the knife to advance or retract, depending on the rotational direction of the third spline 1624c.

In the illustrated embodiment, and as described in more detail below, the activating mechanisms 1638a-c comprise intermeshed gearing assemblies including one or more drive gears driven by rotation of the corresponding spline 1624a-c and configured to drive one or more corresponding driven gears that cause operation of specific functions of the end effector 1604. It is further contemplated herein, however, that the activating mechanisms 1638a-c may be operated through other types of mechanical cooperation such as, but not limited to, belts or cables.

In some embodiments, the drive housing 1614 may include a shroud 1640 sized to receive and otherwise surround the carriage 1626, the lead screw 1622, and the splines 1624a-c. In the illustrated embodiment, the shroud 1640 comprises a tubular or cylindrical structure having a first end 1642a matable with the first end 1618a of the drive housing 1614, and a second end 1642b matable with the second end 1618b of the drive housing 1614. The carriage 1626, the lead screw 1622, and the splines 1624a-c can all be accommodated within the interior of the shroud 1640, and the carriage 1626 may engage and traverse (ride on) one or more rails 1644 (shown in phantom) fixed to the shroud 1640. The rails 1644 extend longitudinally and parallel to the lead screw 1622 and are sized to be received within corresponding notches 1646 defined on the outer periphery of the carriage 1626 and, more particularly, on the outer periphery of one or more of the carriage layers 1628a-e. As the carriage 1626 translates along the longitudinal axis $A_1$, the rails 1644 help maintain the angular position of the carriage 1626 and assume any torsional loading that might otherwise adversely affect movement or operation of the carriage 1626.

Figure 17A:
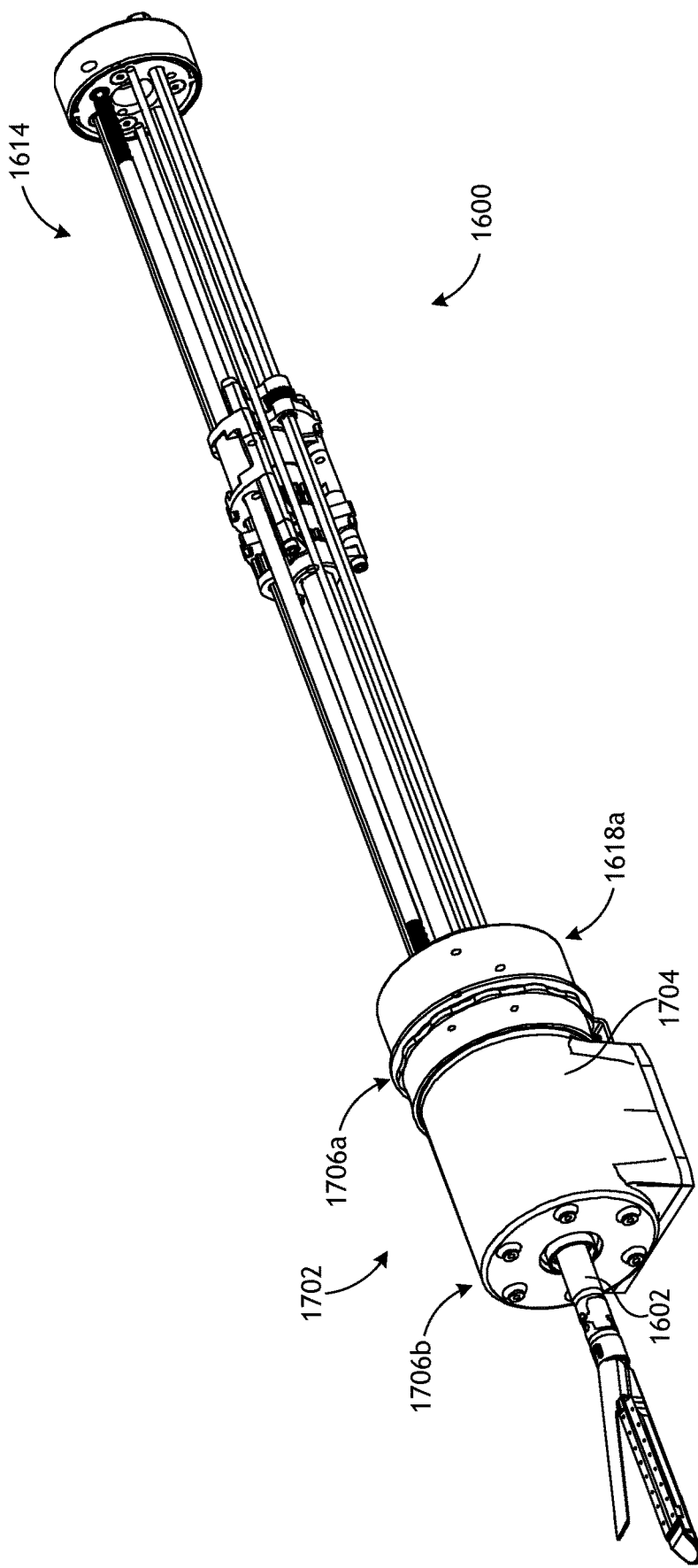
FIG. 17A is an isometric view of the surgical tool of FIG. 16 releasably coupled to an example instrument driver, according to one or more embodiments.

FIG. 17A is an isometric view of the surgical tool 1600 releasably coupled to an example instrument driver 1702, according to one or more embodiments. The instrument driver 1702 may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and designed to provide the motive forces required to operate the surgical tool 1600. Unlike the instrument drivers 1102, 1200, however, the shaft 1602 of the surgical tool 1600 extends through and penetrates the instrument driver 1702.

The instrument driver 1702 has a body 1704 having a first or "proximal" end 1706a and a second or "distal" end 1706b opposite the first end 1706a. In the illustrated embodiment, the first end 1706a of the instrument driver 1702 is matable with and releasably coupled to the first end 1618a of the drive housing 1614, and the shaft 1602 of the surgical tool 1600 extends through the body 1704 and distally from the second end 1706b.

Figure 17B:
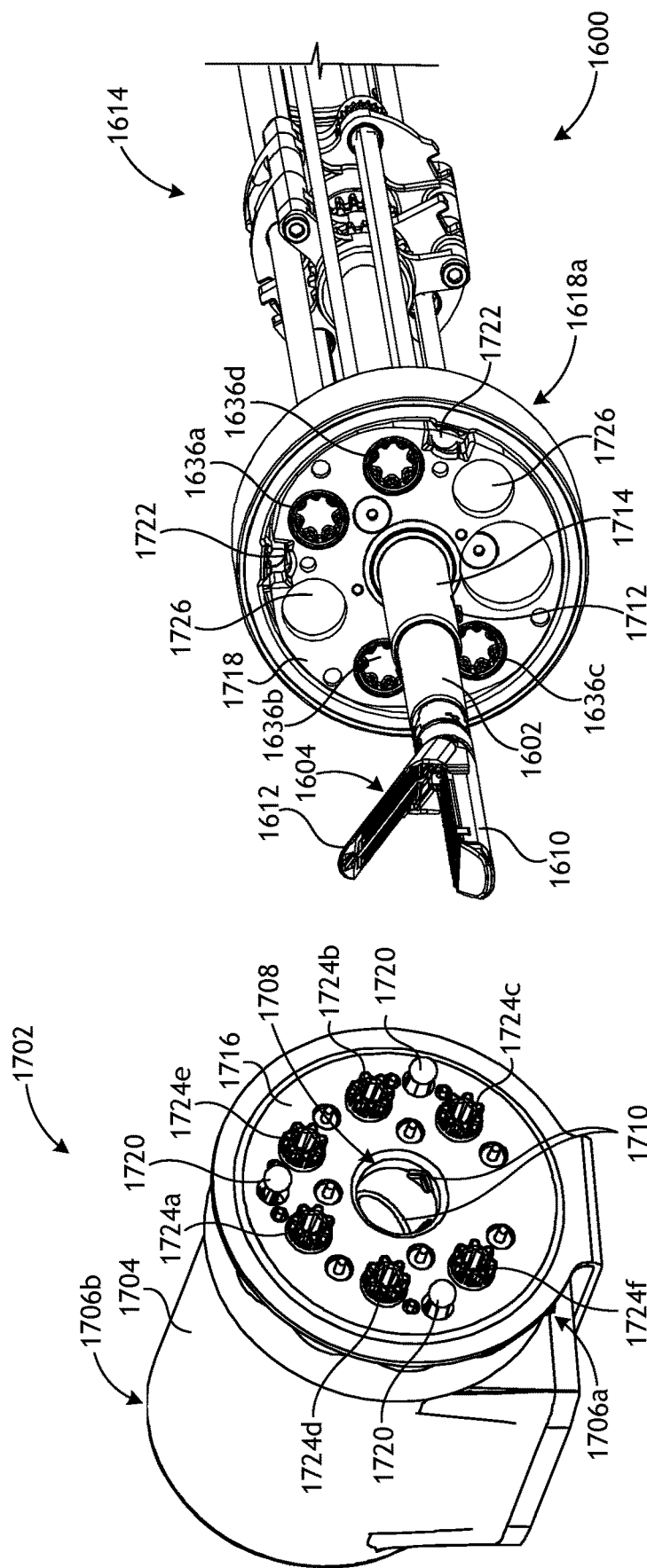
FIG. 17B provides separated isometric end views of the instrument driver and the surgical tool of FIG. 17A.

FIG. 17B depicts separated isometric end views of the instrument driver 1702 and the surgical tool 1600 of FIG. 17A. With the jaws 1610, 1612 closed, the shaft 1602 and the end effector 1604 can penetrate the instrument driver 1702 by extending through a central aperture 1708 defined longitudinally through the body 1704 between the first and second ends 1706a,b. To align the surgical tool 1600 with the instrument driver 1702 in a proper angular orientation, one or more alignment guides 1710 may be provided or otherwise defined within the central aperture 1708 and configured to engage one or more corresponding alignment features 1712 provided on the surgical tool 1600. In the illustrated embodiment, the alignment feature 1712 comprises a protrusion or projection defined on or otherwise provided by an alignment nozzle 1714 extending distally from the first end 1618a of the drive housing 1614. In one or more embodiments, the alignment guide 1710 may comprise a curved or arcuate shoulder or lip configured to receive and guide the alignment feature 1712 as the alignment nozzle 1714 enters the central aperture 1708. As a result, the surgical tool 1600 is oriented to a proper angular alignment with the instrument driver 1702 as the alignment nozzle 1714 is advanced distally through the central aperture 1708. In other embodiments, the alignment nozzle 1714 may be omitted and the alignment feature 1712 may alternatively be provided on the shaft 1602, without departing from the scope of the disclosure.

As illustrated, a drive interface 1716 is provided at the first end 1706a of the instrument driver 1702, and a driven interface 1718 is provided at the first end 1618a of the drive housing 1614. The drive and driven interfaces 1716, 1718 may be configured to mechanically, magnetically, and/or electrically couple the drive housing 1614 to the instrument driver 1702. To accomplish this, the drive and driven interfaces 1716, 1718 may provide one or more matable locating features configured to secure the drive housing 1614 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. The features 1720 may be configured to align and mate with the pockets 1722 via an interference or snap fit engagement, for example.

The instrument driver 1702 also includes one or more drive outputs that protrude from the drive interface 1716 to mate with the drive inputs 1636a-d provided at the first end 1618a of the drive housing 1614. More specifically, the instrument driver 1702 includes a first drive output 1724a matable with the first drive input 1636a, a second drive output 1724b matable with the second drive input 1636b, a third drive output 1724b matable with the third drive input 1636c, and a fourth drive output 1724d matable with the fourth drive input 1636d. In some embodiments, as illustrated, the drive outputs 1724a-d may define splines or features designed to mate with corresponding splined receptacles of the drive inputs 1636a-d. Once properly mated, the drive inputs 1636a-d will share axes of rotation with the corresponding drive outputs 1724a-d to allow the transfer of rotational torque from the drive outputs 1724a-d to the corresponding drive inputs 1636a-d. In some embodiments, each drive output 1724a-d may be spring loaded and otherwise biased to spring outwards away from the drive interface 1716. Moreover, each drive output 1724a-d may be capable of partially or fully retracting into the drive interface 1716.

In some embodiments, the instrument driver 1702 may include additional drive outputs, depicted in FIG. 17B as fifth and sixth drive outputs 1724e, 1724f. The fifth and sixth drive outputs 1724e,f may be configured to mate with additional drive inputs (not shown) of the drive housing 1614 to help undertake one or more additional functions of the surgical tool 1600. The drive housing 1614 does not include additional drive inputs matable with the fifth and sixth drive outputs 1724e,f in the illustrated embodiment. Instead, the driven interface 1718 defines corresponding recesses 1726 configured to receive the fifth and sixth drive outputs 1724e,f. In other applications, however, fifth and/or sixth drive inputs could be included in the drive housing 1614 to mate with the fifth and sixth drive outputs 1724e,f, or the surgical tool 1600 might be replaced with another surgical tool having fifth and/or sixth drive inputs, which would be driven by the fifth and/or sixth drive outputs 1724e,f.

While not shown, in some embodiments, an instrument sterile adapter (ISA) may be placed at the interface between the instrument driver 1702 and the surgical tool 1600. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the surgical tool 1600 to the ISA and simultaneously to the instrument driver 1702.

Figure 18A:
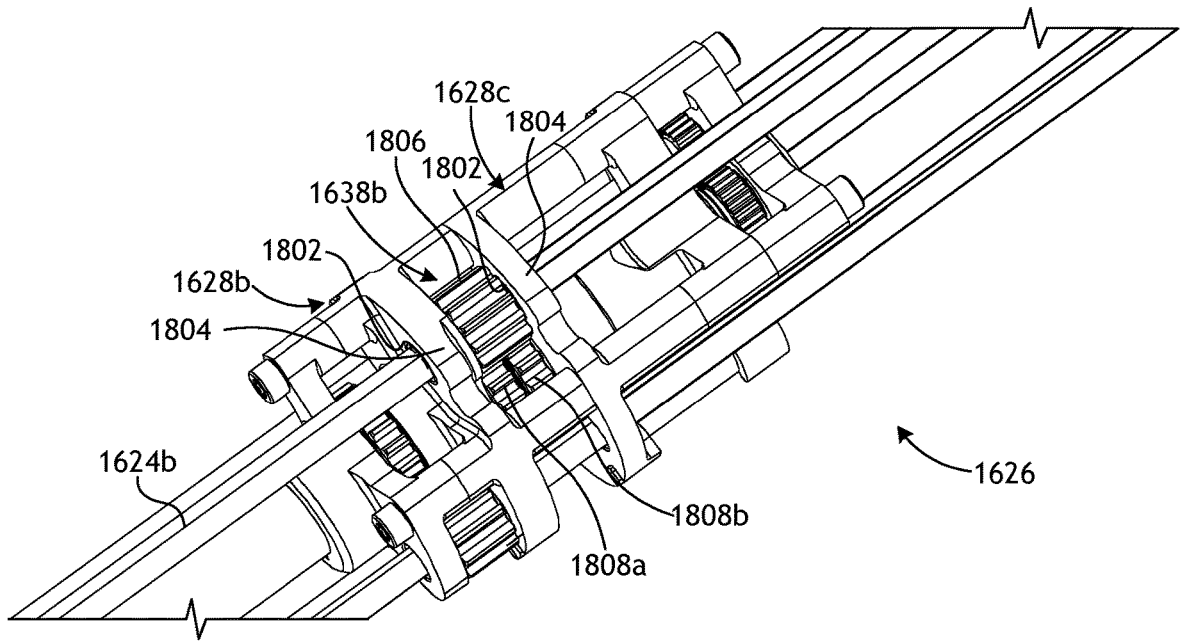
FIGS. 18A and 18B are enlarged isometric and side views, respectively, of the carriage and the second activating mechanism of FIG. 16.

FIG. 18A is an enlarged isometric view of the carriage 1626 and the second activating mechanism 1638b, according to one or more embodiments. As mentioned above, the second spline 1624b can be operatively coupled to the second activating mechanism 1638b such that rotating the second spline 1624b (via rotation of the third drive input 1636c of FIGS. 16 and 17B) will correspondingly actuate the second activating mechanism 1638b and thereby cause the wrist 1606 (FIG. 16) to articulate. As illustrated, the second spline 1624b extends longitudinally through coaxially aligned apertures 1802 defined in the second and third layers 1628b,c of the carriage 1626. In some embodiments, for example, each aperture 1802 may be defined in a corresponding lobe 1804 provided by each of the second and third layers 1628b,c.

A drive gear 1806 may be included with the second spline 1624b and located between the second and third layers 1628b,c and, more particularly, between the lobes 1804 of each layer 1628b,c. The second spline 1624b may exhibit a cross-sectional shape matable with the drive gear 1806 such that rotation of the second spline 1624b correspondingly drives the drive gear 1806 in rotation. In some embodiments, the drive gear 1806 may comprise a separate component part slidably disposed about the second spline 1624b. In such embodiments, as the carriage 1626 moves along the longitudinal axis $A_1$ (FIG. 16), the drive gear 1806 will move along the length of the second spline 1624b as captured between the second and third layers 1628b,c.

The drive gear 1806 may be positioned on the carriage 1626 to simultaneously intermesh with a first or "distal" transfer gear 1808a and a second or "proximal" transfer gear 1808b. Accordingly, as the spline 1624b is rotated, the drive gear 1806 drives the first and second transfer gears 1808a,b simultaneously.

Figure 18B:
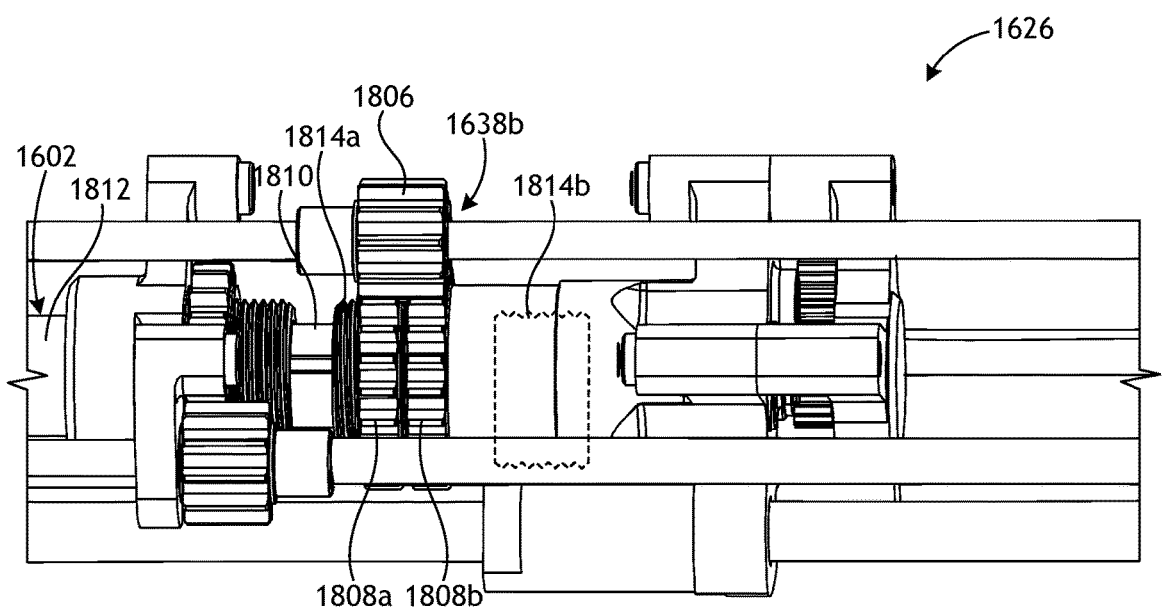

FIG. 18B is an enlarged side view of the carriage 1626 and the second activating mechanism 1638b. The second and third layers 1626b,c (FIG. 18A) of the carriage 1626 are omitted in FIG. 18B to enable a more full view of the second activating mechanism 1638b. The first and second transfer gears 1808a,b may comprise annular structures that extend about the shaft 1602 and, more particularly, about an inner grounding member or shaft 1810 that forms part of the shaft 1602. The inner grounding shaft 1810 extends concentrically within an outer portion of the shaft 1602, referred to herein as a closure tube 1812.

The second activating mechanism 1638b may further include a first or "distal" carrier 1814a (partially visible) and a second or "proximal" carrier 1814b (shown in dashed lines). The first carrier 1814a radially interposes the inner grounding shaft 1810 and at least a portion of the first transfer gear 1808a, and the second carrier 1814b radially interposes the inner grounding shaft 1810 and at least a portion of the second transfer gear 1808b. The first and second transfer gears 1808a,b are internally threaded in opposite directions (i.e., one left-handed and the other right-handed), and the first transfer gear 1808a may threadably engage external threads defined by the first carrier 1814a while the second transfer gear 1808b may threadably engage external threads defined by the second carrier 1814b.

Figure 18C:
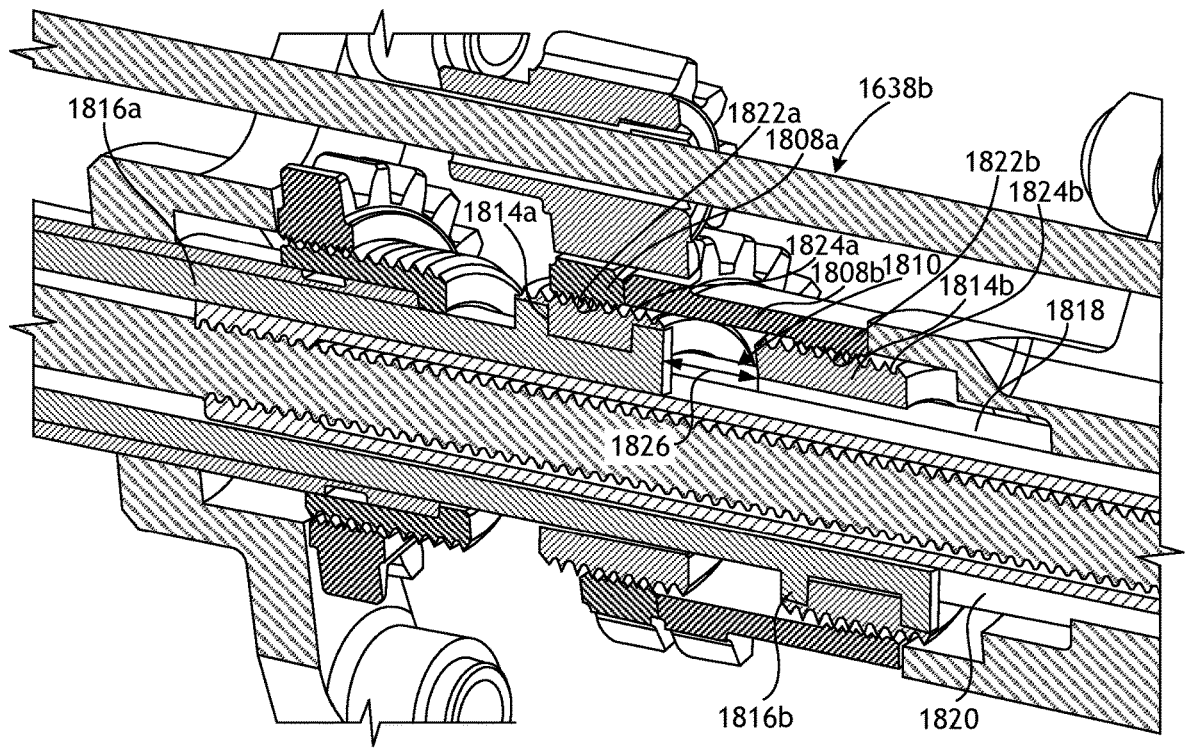
FIG. 18C is an isometric, cross-sectional side view of the second activating mechanism of FIG. 16, according to one or more embodiments.

FIG. 18C is an isometric, cross-sectional side view of the second activating mechanism 1638b, according to one or more embodiments. As illustrated, the first and second carriers 1814a,b radially interpose the inner grounding shaft 1810 and the first and second transfer gears 1808a,b, respectively. Moreover, the first carrier 1814a may be operatively coupled to or otherwise mate with a first drive member 1816a, which extends distally to the wrist 1606 (FIG. 16). The first drive member 1816a is arranged within a corresponding slot 1818 defined in the inner grounding shaft 1810, which guides the first drive member 1816a as it extends to the wrist 1606. Similarly, the second carrier 1814b may be operatively coupled to or otherwise mate with a second drive member 1816b, which extends distally to the wrist 1606. The second drive member 1816b is also arranged within a corresponding slot 1820 defined in the inner grounding shaft 1810, which guides the second drive member 1816b as it extends to the wrist 1606.

The first transfer gear 1808a defines internal threading 1822a matable with external threading 1824a defined on the outer surface of the first carrier 1814a, and the second transfer gear 1808b similarly defines internal threading 1822b matable with external threading 1824b defined on the outer surface of the second carrier 1814b. The internal threadings 1822a,b are oppositely threaded; i.e., one comprises left-handed threads and the other comprises right-handed threads. Consequently, as the drive gear 1806 rotates, it simultaneously drives both transfer gears 1808a,b in rotation, which, in turn, simultaneously drives the corresponding carriers 1814a,b in equal but opposite axial directions because of the oppositely threaded engagement of the internal threadings 1822a,b. Depending on the rotation direction of the drive gear 1806, the carriers 1814a,b may be drawn axially toward each other or moved axially away from each other.

Opposite axial movement of the first and second carriers 1814a,b relative to the inner grounding shaft 1810 and along the longitudinal axis $A_1$ (FIG. 16) correspondingly moves the drive members 1816a,b in the same opposite axial directions and, thereby, articulates the end effector 1604 (FIGS. 16 and 17B). In at least one embodiment, the first and second carriers 1814a,b antagonistically operate such that one of the carriers 1814a,b pulls one of the drive members 1816a,b proximally while the other carrier 1814a,b simultaneously pushes the other drive member 1816a,b distally. A gap 1826 provided between the carriers 1814a,b along the inner grounding shaft 1810 allows the carriers 1814a,b to move toward and away from one another, and thereby provides clearance to facilitate clockwise and counter-clockwise articulation. As the carriers 1814a,b are drawn axially toward each other, the end effector 1604 will articulate in a first direction, and as the carriers 1814a,b are moved axially away from each other, the end effector 1604 will articulate in a second direction opposite the first direction.

Figure 19:
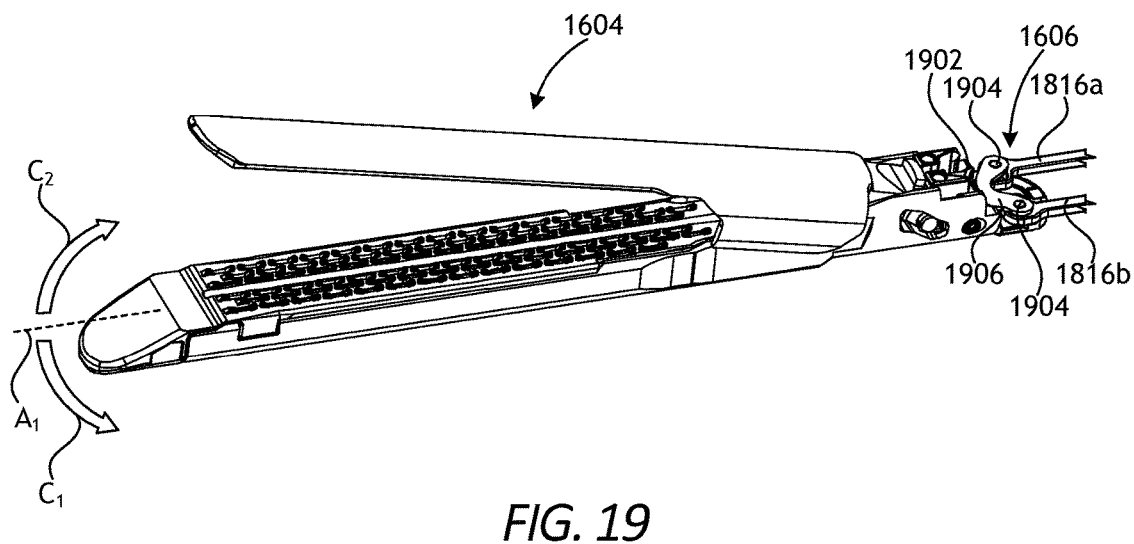
FIG. 19 is an enlarged view of the end effector of FIG. 16 and an exposed view of the wrist of FIG. 16, according to one or more embodiments.

Referring to FIG. 19, with continued reference to FIG. 18C, depicted is an enlarged isometric view of the end effector 1604 and an exposed view of the wrist 1606, according to one or more embodiments. In FIG. 19, the inner grounding shaft 1810 (FIGS. 18B-18C) has been removed to enable viewing of how the drive members 1816a,b interconnect with or are otherwise operatively connected to the end effector 1604. In the illustrated embodiment, the end effector 1604 is mounted to an end effector mount 1902 that defines or otherwise provides two articulation pins 1904, and the distal end of each drive member 1816a,b is rotatably mounted to a corresponding one of the articulation pins 1904. The drive members 1816a,b are also interconnected at the distal ends via a distal link 1906, which together comprise a linkage configured to help articulate end effector mount 1902, and therefore the end effector 1604, in a plane parallel to the longitudinal axis $A_1$.

In this configuration, the drive members 1816a,b translate antagonistically and parallel along the longitudinal axis $A_1$, such that as the first drive member 1816a moves distally the second drive member 1816b moves proximally, and vice versa. Moreover, distal movement of the first drive member 1816a and simultaneous proximal movement of the second drive member 1816b cooperatively act on the end effector mount 1902 to cause the end effector 1604 to rotate counter-clockwise, as indicated by the arrow $C_1$. In contrast, proximal movement of the first drive member 1816a and simultaneous distal movement of the second drive member 1816b cooperatively act on the end effector mount 1902 to cause the end effector 1604 to rotate clockwise, as indicated by the arrow $C_2$.

Figure 20:
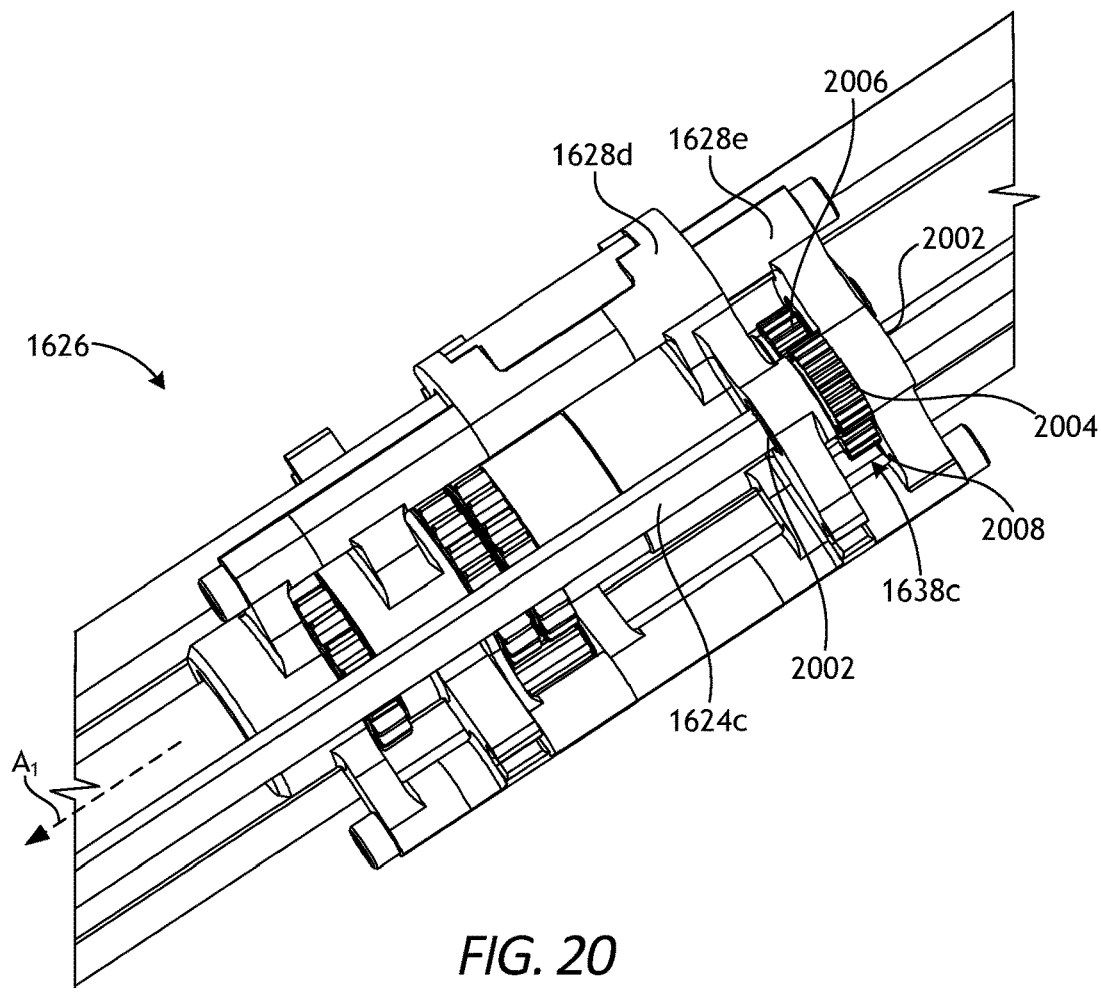
FIG. 20 is another enlarged isometric view of the carriage of FIG. 16.

FIG. 20 is another enlarged isometric view of the carriage 1626 of FIG. 16, and further provides an enlarged view of the third activating mechanism 1638c briefly described above. As mentioned above, the third spline 1624c can be operatively coupled to the third activating mechanism 1638c such that rotating the third spline 1624c (via rotation of the fourth drive input 1636d of FIGS. 16 and 17B) will correspondingly actuate the third activating mechanism 1638c and thereby cause the cutting element (knife) at the end effector 1604 (FIGS. 16, 17B, 19) to "fire". As discussed above, "firing" the end effector 1604 refers to advancing or retracting the cutting element (knife), depending on the rotational direction of the third spline 1624c.

As illustrated, the third spline 1624c extends longitudinally through coaxially aligned apertures 2002 defined in the fourth and fifth layers 1628d,e of the carriage 1626. A drive gear 2004 may be coupled to the third spline 1624c and configured to rotate as the third spline 1624c rotates. As illustrated, the drive gear 2004 may be located between adjacent portions of the fourth and fifth layers 1628d,e. In some embodiments, the drive gear 2004 may comprise a separate component part disposed about the third spline 1624c and capable of translating (sliding) along the third spline 1624c as the carriage 1626 moves along the longitudinal axis $A_1$. In other embodiments, however, the third spline 1624c may be shaped and otherwise configured to operate as the drive gear 2004 to advantageously reduce the number of component parts.

The drive gear 2004 may be configured to drive an input gear 2006 also mounted to the carriage 1626 and forming part of the third activating mechanism 1638c. In some embodiments, the drive gear 2004 may be positioned to directly intermesh with the input gear 2006 and thereby directly drive the input gear 2006 as the third spline 1624c rotates. In other embodiments, however, an idler gear 2008 may interpose the drive gear 2004 and the input gear 2006 and may otherwise transfer torque from the drive gear 2004 to the input gear 2006 via an intermeshed gearing arrangement.

Figure 21:
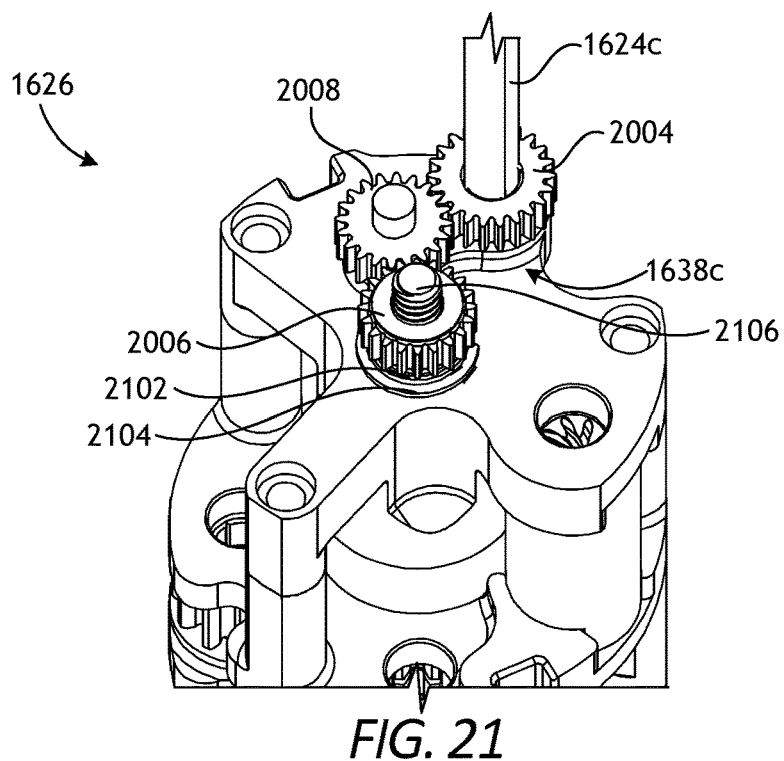
FIG. 21 is an enlarged view of the proximal end of the carriage and the third activating mechanism of FIG. 20.

FIG. 21 is an enlarged view of the proximal end of the carriage 1626 and the third activating mechanism 1638c. Various parts of the carriage 1626 are omitted in FIG. 21, such as the fifth layer 1628e, to enable a fuller view of the third activating mechanism 1638c. As illustrated, the drive gear 2004 is coupled to or forms part of the third spline 1624c and intermeshes with the idler gear 2008, which correspondingly intermeshes with the input gear 2006. In other embodiments, however, the drive gear 2004 may alternatively directly contact and drive the input gear 2006, without departing from the scope of the disclosure.

The input gear 2006 may be rotatably secured to the carriage 1626 with a channel retainer 2102 (only partially visible), and the channel retainer 2102 may be axially fixed to the carriage 1626 with a locking mechanism 2104. In the illustrated embodiment, the locking mechanism 2104 is depicted as a c-ring or an e-ring, but may alternatively comprise any other device or mechanism capable of axially fixing the channel retainer 2102 to the carriage 1626.

The third activating mechanism 1638c further includes a firing rod 2106 longitudinally extendable through the carriage 1626. In at least one embodiment, as illustrated, the firing rod 2106 may also extend at least partially through the input gear 2006. The firing rod 2106 extends along the longitudinal axis $A_1$ (FIG. 20) toward the end effector 1604 (FIGS. 16, 17B, 19) and is operatively coupled to the cutting element (knife) such that longitudinal movement of the firing rod 2106 correspondingly moves the knife in the same direction. In some embodiments, the firing rod 2106 extends to the end effector 1604 and directly couples to the knife. In other embodiments, however, the firing rod 2106 is coupled to a firing member (not shown) at some point between the carriage 1626 and the end effector 1604, and the firing member extends to the end effector 1604 to directly couple to the knife. In either scenario, actuation of the third activating mechanism 1638c causes the knife to "fire", i.e., advance or retract, depending on the rotational direction of the third spline 1624c.

Figure 22:
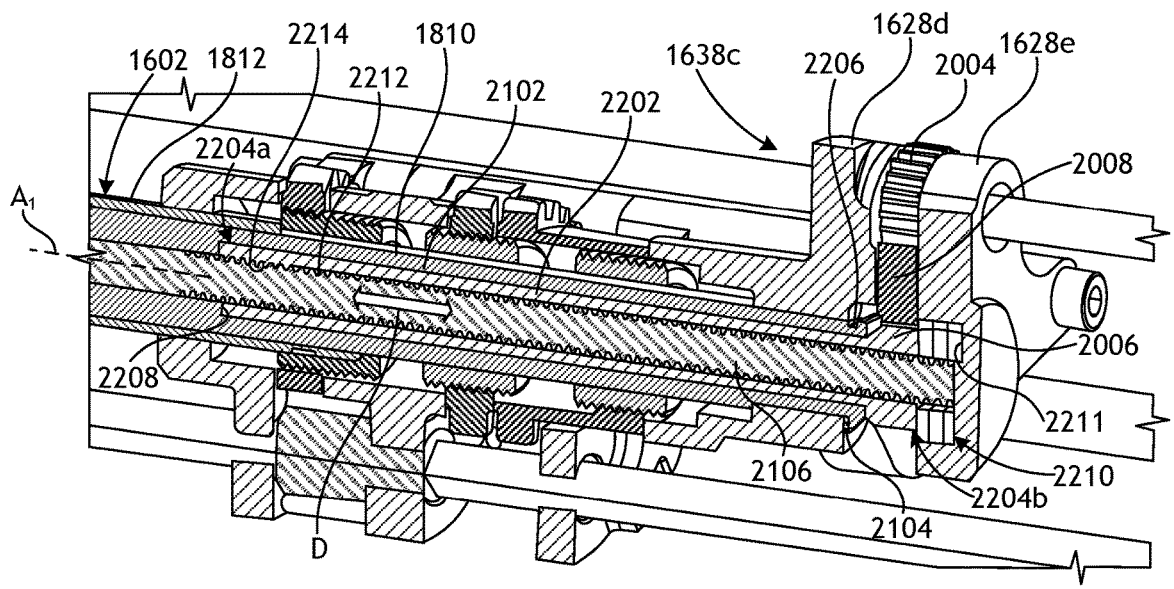
FIG. 22 is an isometric, cross-sectional side view of the third activating mechanism of FIGS. 20 and 21, according to one or more embodiments.

FIG. 22 is an isometric, cross-sectional side view of the third activating mechanism 1638c, according to one or more embodiments. As illustrated, the drive gear 2004 is intermeshed with the idler gear 2008, which correspondingly intermeshes with the input gear 2006. Alternatively, as mentioned above, the drive gear 2004 may directly intermesh with the input gear 2006.

The input gear 2006 may include or may otherwise be coupled to an elongate cylindrical body 2202 that has a first or "distal" end 2204a and a second or "proximal" end 2204b opposite the first end 2204a. As illustrated, the input gear 2006 is located at or near the second end 2204b. The elongate cylindrical body 2202 extends distally from the input gear 2006 within the shaft 1602 and, more particularly, within the inner grounding shaft 1810, which is at least partially arranged within the closure tube 1812. The channel retainer 2102 also extends within the inner grounding shaft 1810 and helps rotatably secure the input gear 2006 and the elongate cylindrical body 2202 to the carriage 1626. As illustrated, the channel retainer 2102 may comprise a cylindrical member sized to receive the elongate cylindrical body 2202 within its interior. The channel retainer 2102 may be axially fixed to the carriage 1626 with the locking mechanism 2104, which may be received within a groove 2206 defined on the proximal end of the channel retainer 2102.

The channel retainer 2102 may provide or otherwise define an inner radial shoulder 2208 configured to engage the first end 2204*a* of the elongate cylindrical body 2202 and thereby prevent the elongate cylindrical body 2202 from moving distally. At the second end 2204*b* of the elongate cylindrical body 2202, the channel retainer 2102 bears against one axial side (i.e., the distal end) of the input gear 2006, while one or more thrust bearings 2210 (three shown) bear against the opposite axial side (i.e., the proximal end) of the input gear 2006. In one or more embodiments, the thrust bearings 2210 may be received within a pocket 2211 defined in the fifth layer 1628*e*, and secured in place as the fifth layer 1628*e* is coupled to the fourth layer 1628*d*. Consequently, the input gear 2006 is secured axially in place between the channel retainer 2102 and the thrust bearings 2210 but simultaneously allowed to rotate about the longitudinal axis $A_1$. The thrust bearings 2210 may be configured to assume axial loading on the input gear 2006 as the third activating mechanism 1638*c* is actuated. The thrust bearings 2210 may also prove advantageous in reducing rotational friction of the input gear 2006 while driving (firing) the firing rod 2106.

Some or all of the firing rod 2106 may provide or otherwise define external threads 2212 configured to threadably engage internal threads 2214 provided at or near the first end 2204*a* of the elongate cylindrical body 2202. In example operation of the third activating mechanism 1638*c*, the third spline 1624*c* is rotated (via rotation of the fourth drive input 1636*d* of FIGS. 16 and 17B) and the drive gear 2004 correspondingly rotates to drive the input gear 2006 (either directly or through the idler gear 2008). Rotating the input gear 2006 correspondingly rotates the elongate cylindrical body 2202 in the same angular direction, which drives the internal threads 2214 of the body 2202 against the external threads 2212 of the firing rod 2106, and thereby advances or retracts the firing rod 2106 along the longitudinal axis $A_1$, as indicated by the arrows D. Longitudinal movement of the firing rod 2106 correspondingly moves the knife in the same direction at the end effector 1604 (FIGS. 16, 17B, 19).

Figure 23:
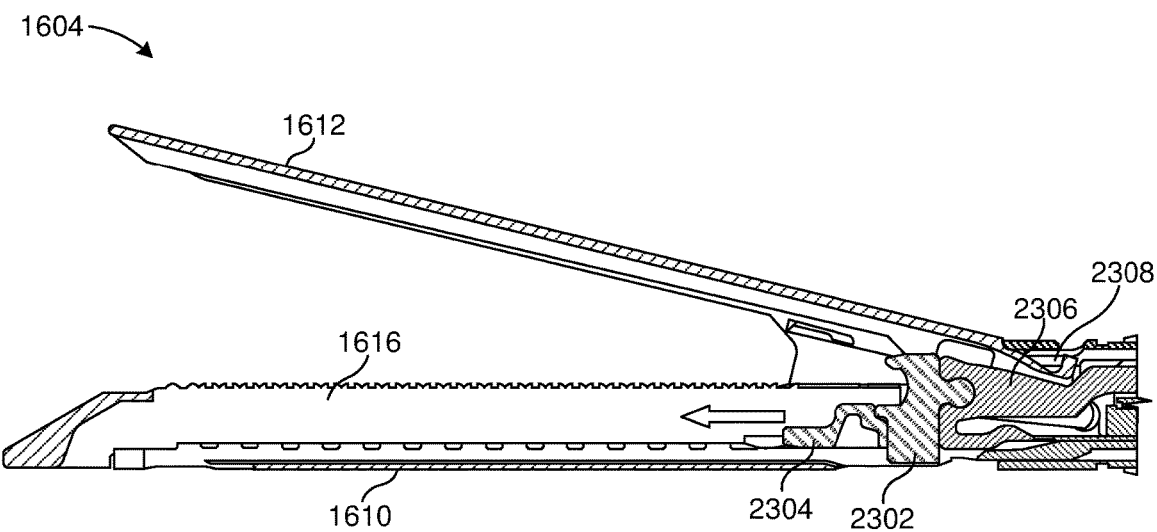
FIG. 23 is an enlarged cross-sectional view of the end effector of FIG. 16, according to one or more embodiments.

Referring to FIG. 23, with continued reference to FIG. 22, depicted is an enlarged cross-sectional view of the end effector 1604, according to one or more embodiments. As mentioned above, the end effector 1604 includes opposing jaws 1610, 1612 movable between open and closed positions, and the jaws 1610, 1612 are depicted in FIG. 23 in the open position. The end effector 1604 may further include a knife 2302 that can be linearly displaced within the slot 1616 defined in the second jaw 1610 to cut tissue grasped between the jaws 1610, 1612. As the knife 2302 advances distally within the slot 1616, a sled or camming wedge 2304 simultaneously engages a plurality of staples (not shown) contained within the first jaw 1610 (e.g., within a staple cartridge) and urges (cams) the staples into deforming contact with the opposing anvil surfaces (e.g., pockets) provided on the second jaw 1612. Properly deployed staples help seal opposing sides of the transected tissue.

As illustrated, the knife 2302 is operatively coupled to a firing member 2306 that extends proximally (i.e., to the right in FIG. 23) and is operatively coupled to the firing rod 2106 of FIGS. 21-22 at its proximal end. In other embodiments, however, the knife 2302 may be directly coupled to the firing rod 2106, without departing from the scope of the disclosure. Actuation of the firing rod 2106, as generally described above, causes the firing member 2306 to advance and retract and correspondingly advance and retract the knife 2302 so that it can transect tissue grasped between the jaws 1610, 1612. Distal movement of the firing member 2306 also correspondingly moves the camming wedge 2304 to deploy the staples, as described above.

In some embodiments, movement of the firing rod 2106 (FIGS. 21-22) in the distal direction may also cause the jaws 1610, 1612 to close. More specifically, in one or more embodiments, the firing rod 2106 (or the firing member 2306) or the knife 2302 may include a feature or structure (not shown) configured to engage an anvil 2708 provided on the upper jaw 1612. In such embodiments, as the firing rod 2106 is advanced distally, the feature or structure will axially engage the angled surface of the anvil 2708 and force the second jaw 1612 to close. This approach is commonly referred to as "knife-based" closure, and in such embodiments, the jaws 1610, 1612 may be spring biased to the open position when the knife 2302 is fully retracted. In other embodiments, however, as the firing rod 2106 is advanced distally, the closure tube 1812 (FIG. 22) may be simultaneously advanced in the same direction to engage the anvil 2708 and force the second jaw 1612 to close. This approach is commonly referred to as "tube-based" closure.

Figure 24A:
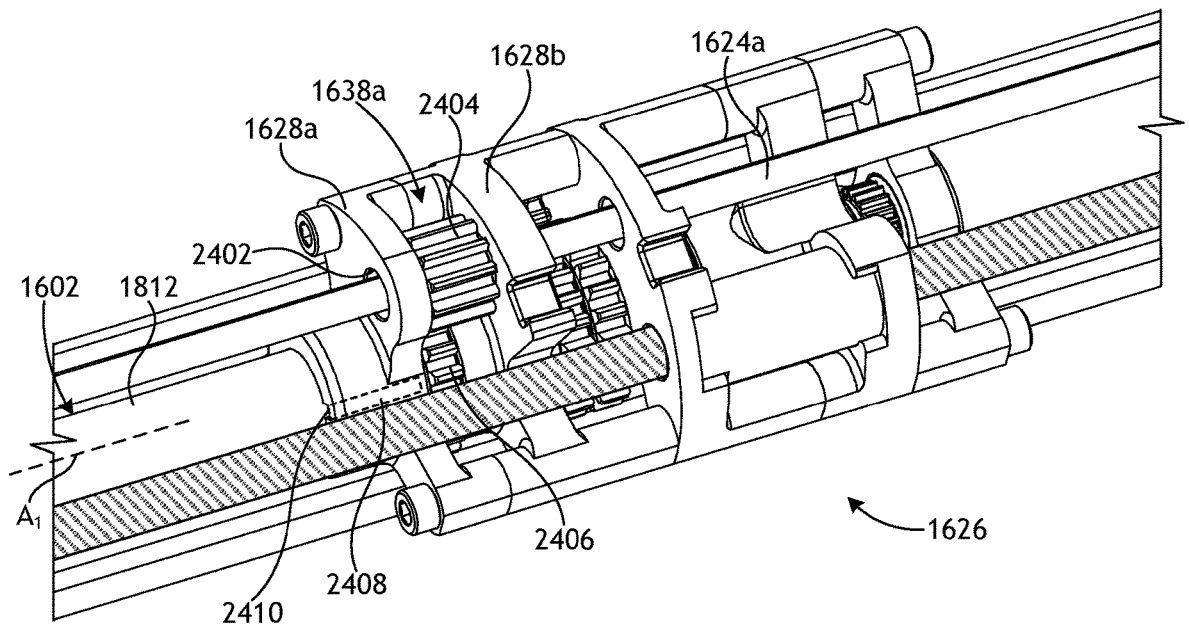
FIG. 24A is an enlarged isometric view of another embodiment of the carriage of FIG. 16.

FIG. 24A is an enlarged isometric view of another embodiment of the carriage 1626 of FIG. 16, and further provides an enlarged view of at least one embodiment of the first activating mechanism 1638*a* briefly described above. As mentioned herein, the first activating mechanism 1638*a* may be actuated or otherwise activated to open or close the jaws 1610, 1612 (FIGS. 16 and 17B) at the end effector 1604 (FIGS. 16 and 17B). More specifically, the first spline 1624*a* may be operatively coupled to the first activating mechanism 1638*a* such that rotating the first spline 1624*a* (via rotation of the second drive input 1636*b* of FIGS. 16 and 17B) will correspondingly actuate the first activating mechanism 1638*a* and thereby open or close the jaws 1610, 1612, depending on the rotational direction of the first spline 1624*a*.

As illustrated, the first spline 1624*a* extends longitudinally through coaxially aligned apertures 2402 (only one visible) defined in the first and second layers 1628*a,b* of the carriage 1626. A drive gear 2404 may be included with the first spline 1624*a* and located between adjacent portions of the first and second layers 1628*a,b*. The first spline 1624*a* may exhibit a cross-sectional shape matable with a corresponding inner shape of the drive gear 2404 such that rotation of the first spline 1624*a* correspondingly drives the drive gear 2404 in rotation. In some embodiments, the drive gear 2404 may comprise a separate component part slidably disposed about the outer surface of the first spline 1624*a*. In such embodiments, as the carriage 1626 moves along the longitudinal axis $A_1$ (FIG. 16), the drive gear 2404 will correspondingly move along the length of the first spline 1624*a* as captured between the first and second layers 1628*a,b*. In other embodiments, however, the first spline 1624*a* may be shaped and otherwise configured to operate as a drive gear. In such embodiments, the drive gear 2404 may be omitted to advantageously reduce the number of component parts.

The first activating mechanism 1638a may include a driven gear 2406, and the drive gear 2404 may be positioned on the carriage 1626 to engage or otherwise intermesh with the driven gear 2406. In other embodiments, however, one or more intermediate gears (e.g., idler gears) may interpose the drive gear 2404 and the driven gear 2406. Accordingly, as the first spline 1624a is rotated, the drive gear 2404 is able to drive the driven gear 2406 in rotation and thereby actuate the first activating mechanism 1638a. As illustrated, the driven gear 2406 may also be located between adjacent portions of the first and second layers 1628a,b of the carriage 1626.

The first activating mechanism 1638a may further include a key 2408 (shown in dashed lines) provided or otherwise defined on the outer surface of the shaft 1602 and, more particularly, on the outer surface of the closure tube 1812 of the shaft 1602. The key 2408 may be received within a slot 2410 defined in the carriage 1626 and, more particularly, in the first layer 1628a. In the illustrated embodiment, the key 2408 is depicted as an elongate member or protrusion, and the slot 2410 may define an opening sized to receive the key 2408. Actuating the first activating mechanism 1638a causes the closure tube 1812 to translate along the longitudinal axis $A_1$, which correspondingly causes the key 2408 to translate longitudinally within the slot 2410. With the key 2408 received within the slot 2410, the closure tube 1812 is prevented from rotating during longitudinal movement of the closure tube 1812 resulting from actuation of the first activating mechanism 1638a.

Figure 24B:
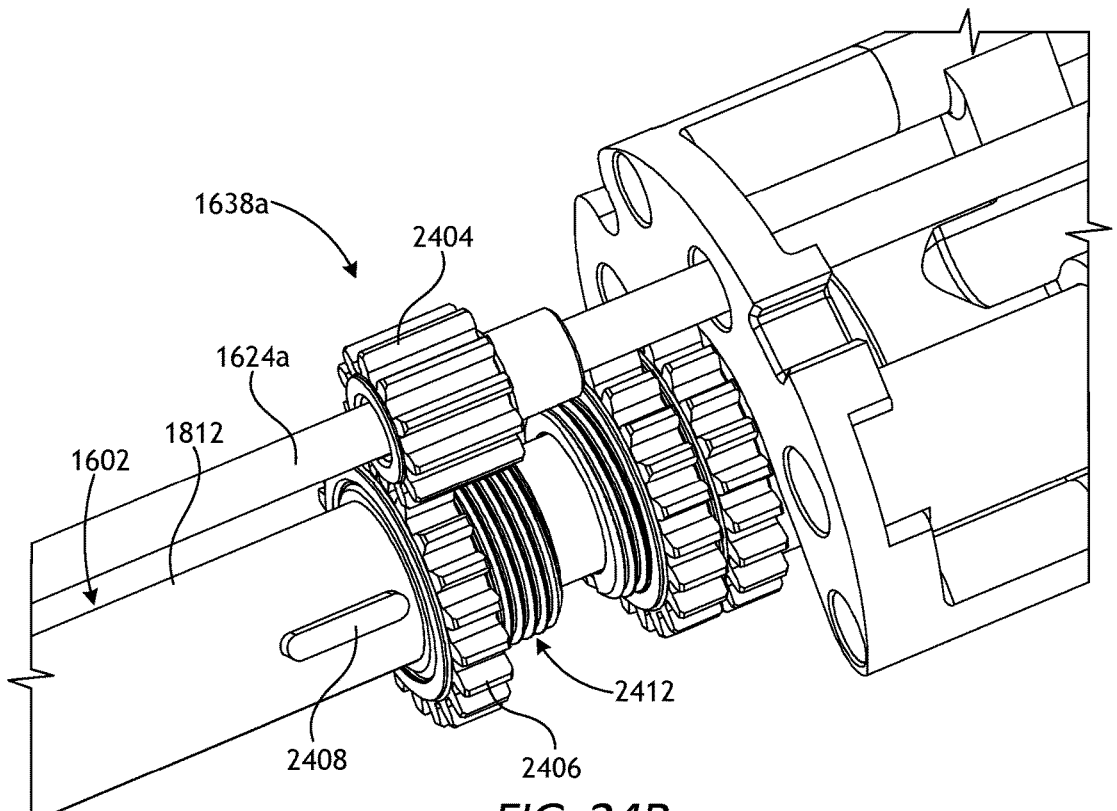
FIG. 24B is an enlarged isometric view of the first activating mechanism of FIG. 24A, according to one or more embodiments.

FIG. 24B is an enlarged isometric view of the first activating mechanism 1638a, according to one or more embodiments. Various parts of the carriage 1626, including the first and second layers 1626a,b (FIG. 24A), are omitted in FIG. 24B to enable a fuller view of the first activating mechanism 1638a. As illustrated, the driven gear 2406 may comprise an annular structure that extends about the closure tube 1812 of the shaft 1602, and the key 2408 is depicted as coupled to or otherwise defined on the outer surface of the closure tube 1812. Moreover, the gear teeth of the driven gear 2406 intermesh with gear teeth of the drive gear 2404 to enable the drive gear 2404 to rotate the driven gear 2406 when the first spline 1624a is rotated.

The first activating mechanism 1638a may further include a carrier 2412 arranged at the proximal end of the closure tube 1812. The driven gear 2406 is internally threaded and configured to threadably engage external threads defined by the carrier 2412. Consequently, as the drive gear 2404 rotates, the driven gear 2406 correspondingly rotates and moves the closure tube 1812 along the longitudinal axis $A_1$ (FIG. 24A) via the threaded engagement between the driven gear 2406 and the carrier 2412. Depending on the rotation direction of the drive gear 2404, the closure tube 1812 may be driven distally (i.e., to the left in FIG. 24B) or proximally (i.e., to the right in FIG. 24B).

In some embodiments, the carrier 2412 may form an integral part of the closure tube 1812 and thereby constitute the proximal end of the shaft 1602. In such embodiments, the proximal end of the shaft 1602 may be threaded to form the carrier 2412. In other embodiments, however, the carrier 2412 may comprise a separate component part arranged at the proximal end of the closure tube 1812. In such embodiments, the carrier 2412 may be configured to receive the proximal end of the closure tube 1812 and may radially interpose a portion of the closure tube 1812 and the driven gear 2406. In either scenario, movement of the carrier 2412 along the longitudinal axis $A_1$ (FIG. 24A), will correspondingly move the closure tube 1812 in the same axial direction.

Figure 24C:
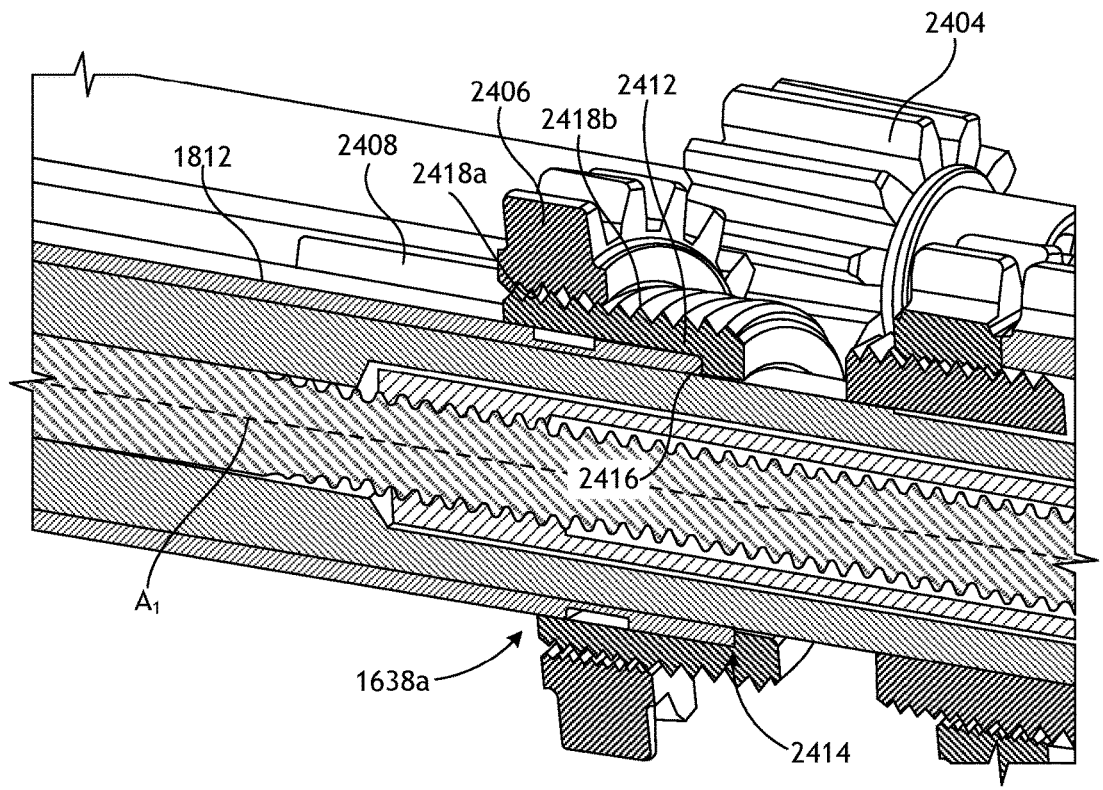
FIG. 24C is an isometric, cross-sectional side view of the first activating mechanism of FIGS. 24A-24B.

FIG. 24C is an isometric, cross-sectional side view of the first activating mechanism 1638a, according to one or more embodiments. In the illustrated embodiment, the carrier 2412 comprises a separate component part arranged at a proximal end 2414 of the closure tube 1812 and radially interposes a portion of the closure tube 1812 and the driven gear 2406. In such embodiments, the carrier 2412 may define an inner radial shoulder 2416 engageable with the proximal end 2414 of the closure tube 1812. As mentioned above, however, the carrier 2412 may alternatively form an integral part of the closure tube 1812 at the proximal end 2414, without departing from the scope of the disclosure.

The driven gear 2406 defines internal threading 2418a matable with external threading 2418b defined on the outer surface of the carrier 2412. As the driven gear 2406 is driven to rotate about the longitudinal axis $A_1$, the threaded engagement between the internal and external threadings 2418a,b causes the carrier 2412 to axially advance or retract along the longitudinal axis $A_1$, and correspondingly advance or retract the closure tube 1812 in the same axial direction. As the carrier 2412 advances distally (i.e., to the left in FIG. 24C), the inner radial shoulder 2416 bears against the proximal end 2414 of the closure tube 1812 and thereby forces the closure tube 1812 in the same distal direction. Advancing the closure tube 1812 distally forces the jaws 1610, 1612 (FIGS. 16 and 17B) to close, and retracting the closure tube 1812 proximally (i.e., to the right in FIG. 24C) allows the jaws 1610, 1612 to open.

Figure 25:
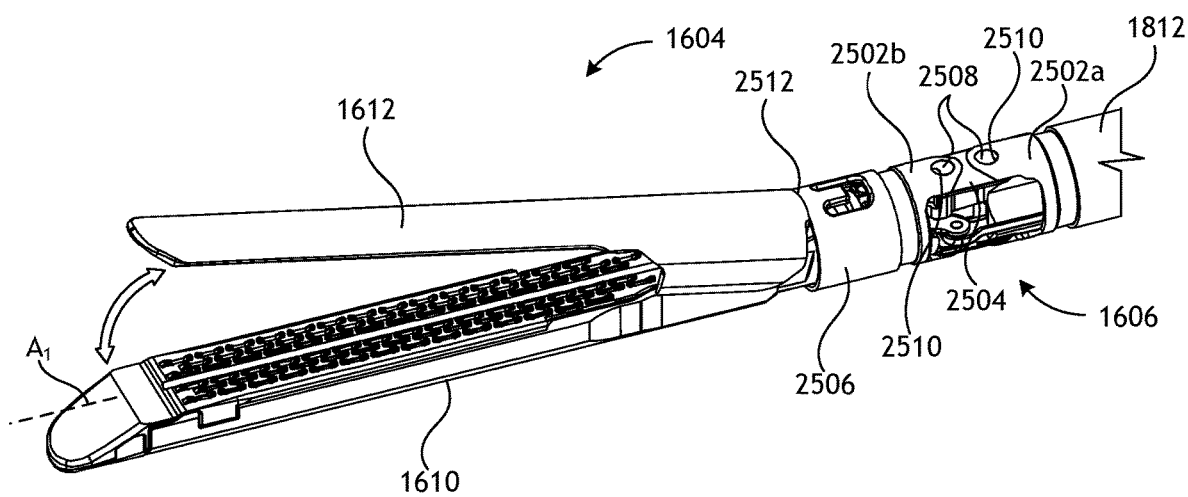
FIG. 25 is an enlarged view of the end effector and the wrist of FIG. 16, according to one or more embodiments.

Referring to FIG. 25, with continued reference to FIG. 24C, depicted is an enlarged view of the end effector 1604 and the wrist 1606, according to one or more embodiments. As illustrated, the wrist 1606 may include a first or "proximal" clevis 2502a, a second or "distal" clevis 2502b, and a closure link 2504 configured to operatively couple the proximal and distal devises 2502a,b across the wrist 1606. The proximal clevis 2502a may be coupled to or otherwise form part of the distal end of the closure tube 1812, and the distal clevis 2502b may be coupled to or otherwise form part of a closure ring 2506.

Axial movement of the closure tube 1812 along the longitudinal axis $A_1$, as generally described above, correspondingly moves the proximal clevis 2502a in the same axial direction, and the closure link 2504 is configured to transmit the axial load through (across) the wrist 1606 to close the jaws 1610, 1612 of the end effector 1604. More specifically, the closure link 2504 defines a pair of protrusions 2508 configured to mate with corresponding apertures 2510 defined in each of the proximal and distal devises 2502a,b. The closure link 2504 may transmit the closure load or translation of the closure tube 1812 from the distal clevis 2502b to the proximal clevis 2502a and the closure ring 2506 will correspondingly push or pull on the upper jaw 1612 to open or close the upper jaw 1612. To close the upper jaw 1612, the closure ring 2506 is forced against a shoulder 2512 at or near the back of the upper jaw 1612, which urges the upper jaw 1612 to pivot down and to the closed position. To open the upper jaw 1612, the closure ring 2506 is retracted proximally by retracting the closure tube 1812, and the closure ring 2506 helps pull the upper jaw 1612 back toward the open position. Alternatively, the upper jaw 1612 may be spring loaded and biased to the open position, and retracting the closure ring 2506 removes loading on the shoulder 2512, which allows the spring force to move the upper jaw 1612 to the open position.

Figure 26:
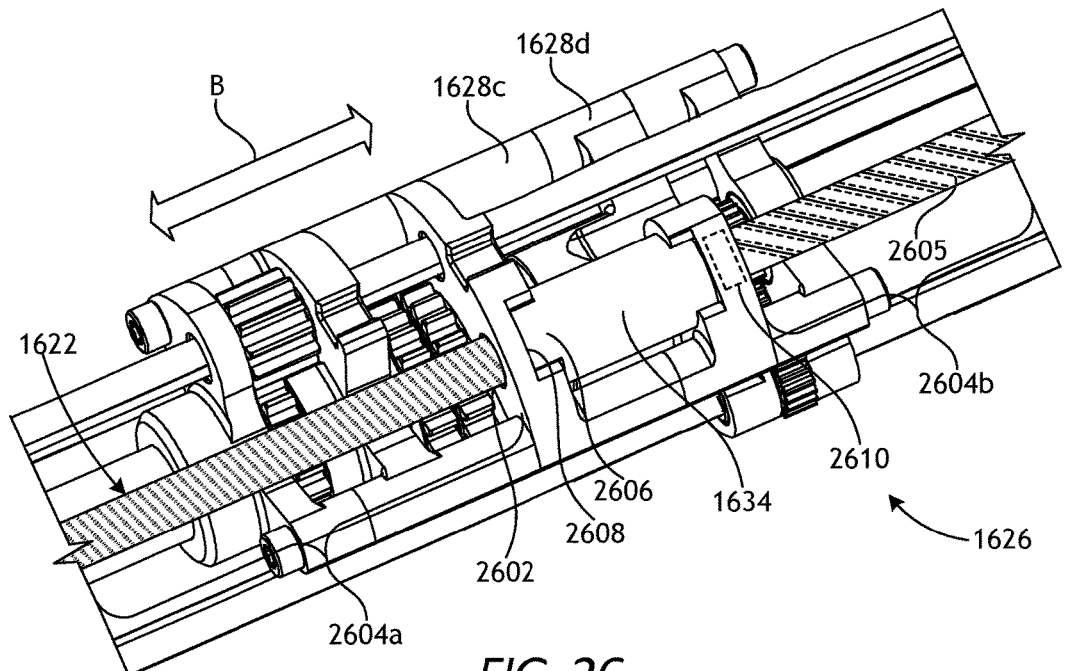
FIG. 26 is another enlarged isometric view of the carriage of FIG. 16.

FIG. 26 is another enlarged isometric view of the carriage 1626 of FIG. 16. As discussed with reference to FIG. 16, the shaft 1602 is coupled to and extends distally from the carriage 1626 and penetrates the first end 1618a (FIG. 16) of the drive housing 1614 (FIG. 16). Moreover, the carriage 1626 is movable between the first and second ends 1618a,b (FIG. 16) along the longitudinal axis $A_1$ to advance or retract the end effector 1604 (FIG. 16) relative to the drive housing 1614, as indicated by the arrows B (i.e., z-axis translation).

In one or more embodiments, as briefly discussed above, axial translation of the carriage 1626 may be accomplished through the use and mechanical interaction of the lead screw 1622 and the carriage nut 1634. As illustrated, the carriage 1626 may be at least partially mounted to the lead screw 1622 by having the lead screw 1622 extend through one or more portions of the carriage 1626, such as adjacent portions of the third and fourth layers 1628c,d. In the illustrated embodiment, the lead screw 1622 extends through co-axially aligned apertures 2602 (only one shown) defined in adjacent portions of the third and fourth layers 1628c,d.

The carriage 1626 is configured to traverse the axial length of the lead screw 1622 by mechanical interaction with the carriage nut 1634. More particularly, the outer surface of the lead screw 1622 defines outer helical threading and the carriage nut 1634 defines corresponding internal helical threading (not shown) matable with the outer helical threading of the lead screw 1622. The carriage nut 1634 is immovably secured to the carriage 1626 such that rotation of the lead screw 1622 causes the carriage nut 1634 to convert the rotational force of the lead screw 1622 into an axial load applied to the carriage 1626. Consequently, the carriage nut 1634 is urged to traverse the outer helical threading of the lead screw 1622 and thereby advance or retract the carriage 1626 along the longitudinal axis $A_1$ in the direction(s) B. As the carriage 1626 moves along the longitudinal axis $A_1$, the end effector 1604 (FIG. 16) correspondingly advances or retracts relative to the drive housing 1614. Depending on the rotational direction of the lead screw 1622, the carriage 1626 and the end effector 1604 may be moved distally (i.e., to the left in FIG. 26) or proximally (i.e., to the right in FIG. 26).

In some embodiments, the outer helical threading of the lead screw 1622 may be uniform (constant) along the entire length of the lead screw 1622. In such embodiments, the outer helical threading will be provided (defined) at a single common pitch between both ends of the lead screw 1622. In other embodiments, however, the pitch of the outer helical threading may vary along portions of the lead screw 1622. As illustrated, for example, a first portion 2604a of the lead screw 1622 may provide outer helical threading defined at a first pitch, while a second portion 2604b of the lead screw 1622 may provide outer helical threading defined at a second pitch different from the first pitch. In the illustrated embodiment, the second pitch defined on the second portion 2604b is more aggressive as compared to the first pitch defined on the first portion 2604a. As a result, while the lead screw 1622 is rotated at a constant speed, the carriage 1626 will move along the longitudinal axis $A_1$ at a faster speed while traversing the second portion 2604b as compared to traversing the first portion 2604a. This may prove advantageous in allowing the operator to advance the end effector (FIG. 16) toward a surgical site faster along select portions of the lead screw 1622.

The lead screw 1622 may be made of a variety of rigid materials including, but not limited to, a plastic (e.g., an extruded polymer), a metal (e.g., aluminum, stainless steel, brass, etc.), a composite material (e.g., carbon fiber, fiberglass, etc.), or any combination thereof. The lead screw 1622 may exhibit a surface finish or include a coating that reduces friction against the carriage nut 1634 when the carriage 1626 is under loading, i.e., twisting or compressive loads. In at least one embodiment, for instance, the outer helical threading of the lead screw 1622 may be coated with a lubricant or lubricious substance 2605, such as polytetrafluoroethylene (PTFE or TEFLON®). In other embodiments, or in addition thereto, the outer helical threading of the lead screw 1622 may be anodized or otherwise exhibit an anodized outer surface.

In some embodiments, as illustrated, the carriage nut 1634 may comprise a separate component part mounted to the lead screw 1622 and secured to the carriage 1626, such as between adjacent portions of the third and fourth layers 1628c,d. In such embodiments, the carriage nut 1634 may provide or otherwise define an anti-rotation feature 2606 matable with a corresponding feature 2608 defined on the carriage 1626. The anti-rotation feature 2606 may be configured to transfer rotational loading assumed by the carriage nut 1634 through rotation of the lead screw 1622 to the carriage 1626. As a result, the rotational loading can be converted into axial loading that helps move the carriage 1626 along the longitudinal axis $A_1$. In the illustrated embodiment, the anti-rotation feature 2606 comprises a flange and the feature 2608 comprises a pocket or recess configured to receive the flange.

In other embodiments, however, the carriage nut 1634 may form an integral part of the carriage 1626. In such embodiments, one or both of the third and fourth layers 1628c,d may operate as the carriage nut 1634. More specifically, the carriage nut 1634 may be arranged within one or both of the co-axially aligned apertures 2602, as indicated by the dashed box 2610. Alternatively, one or both of the co-axially aligned apertures 2602 may be internally threaded to mate with the outer helical threading of the lead screw 1622. In such embodiments, rotation of the lead screw 1622 will correspondingly drive the carriage 1626 distally or proximally as threadably interacting with the threaded aperture(s) 2602.

Figure 27A:
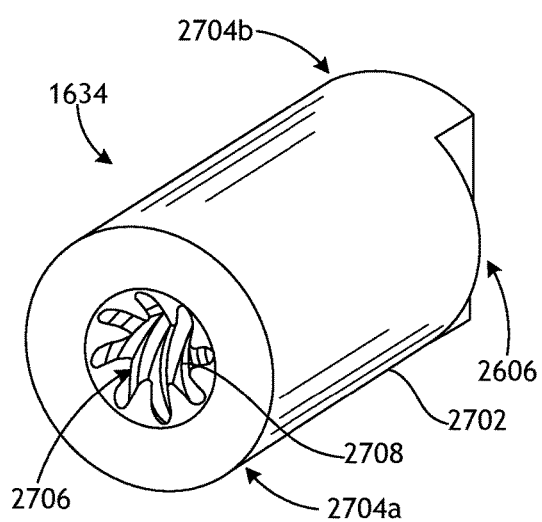
FIGS. 27A and 27B are isometric end views of the carriage nut of FIGS. 16 and 26, according to one or more example embodiments.
Figure 27B:
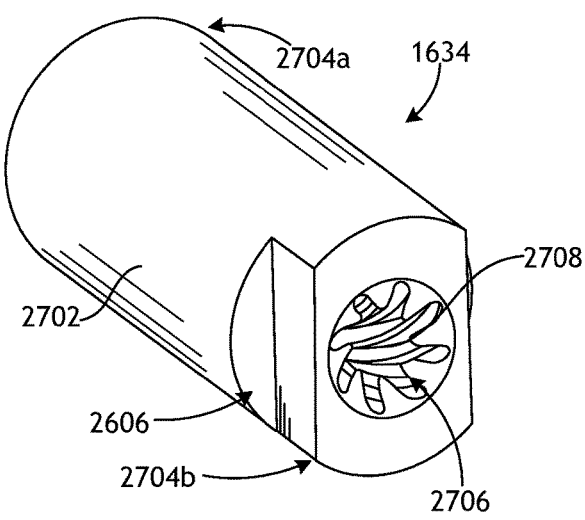

FIGS. 27A and 27B are opposing isometric end views of the carriage nut 1634, according to one or more embodiments. As illustrated, the carriage nut 1634 provides a generally cylindrical body 2702 having a first end 2704a and a second end 2704b opposite the first end 2704a. A central conduit 2706 may be defined in the body 2702 and extend between the first and second ends 2704a,b. As illustrated, internal helical threading 2708 may be defined on the inner wall of the central conduit 2706 and may be configured to threadably mate with the external helical threading defined on the lead screw 1622 (FIG. 26).

In some embodiments, one or both of the ends 2704a,b may provide or otherwise define the anti-rotation feature 2606 configured to prevent the carriage nut 1634 from rotating while traversing the lead screw (FIG. 26). In the illustrated embodiment, the anti-rotation feature 2606 is provided at the second end 2704b, but could alternatively be provided at the first end 2704a or both ends 2704a,b. Once the anti-rotation feature 2606 is received within the corresponding feature 2608 (FIG. 26) defined on the carriage 1626 (FIG. 26), the carriage nut 1634 will be prevented from rotating relative to the carriage 1626, which allows the rotational force from the lead screw 1622 to be transferred through the carriage nut 1634 to the carriage 1626 in the form of an axial load that causes axial movement of the carriage 1626.

Figure 28A:
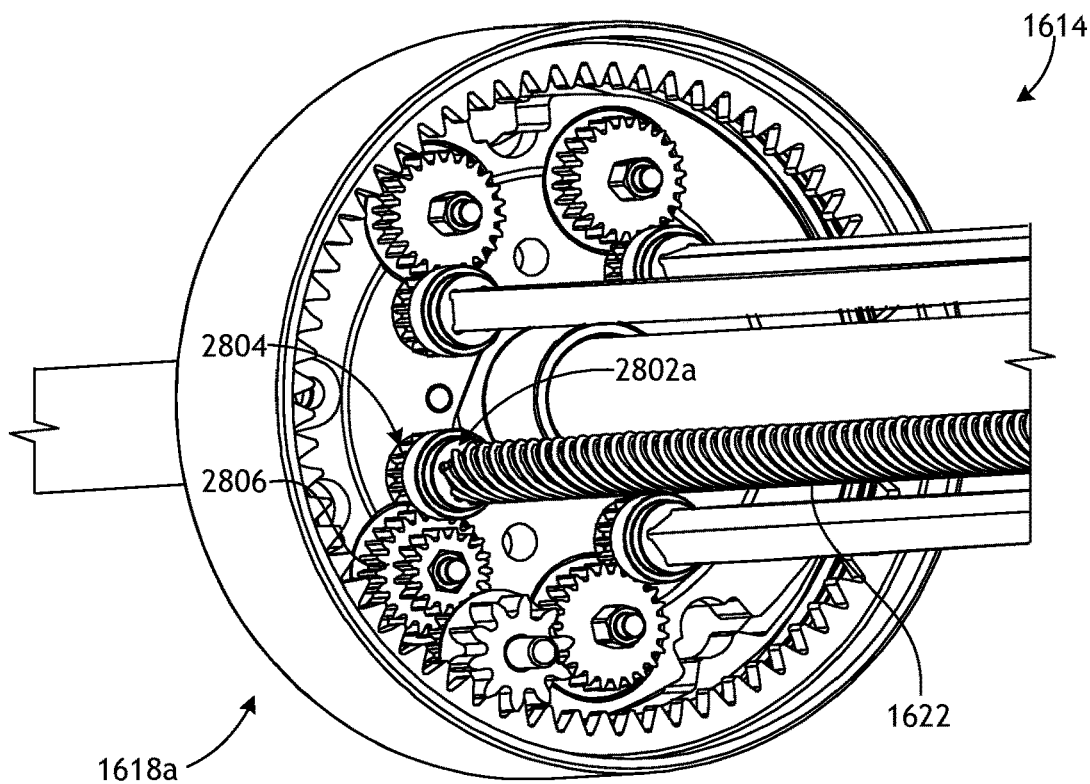
FIGS. 28A and 28B are isometric views of the first and second ends, respectively, of the handle of FIG. 16, according to one or more embodiments.
Figure 28B:
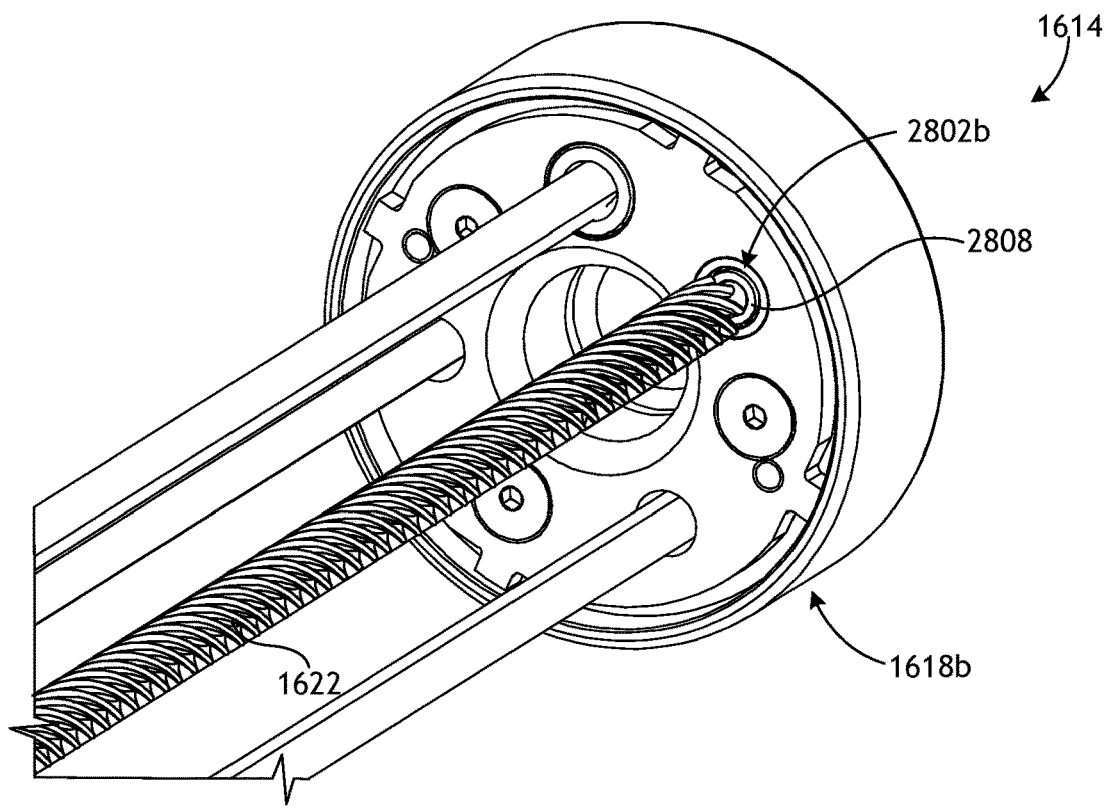

FIGS. 28A and 28B are isometric views of the first and second ends 1618a,b, respectively, of the drive housing 1614 of FIG. 16, according to one or more embodiments. The lead screw 1622 extends between and is rotatably mounted to the first and second ends 1618a,b of the drive housing 1614.

More specifically, a first or "distal" end 2802*a* (FIG. 28A) of the lead screw 1622 is rotatably mounted to the first end 1618*a* of the drive housing 1614, and a second or "proximal" end 2802*b* (FIG. 28B) of the lead screw 1622 is rotatably mounted to the second end 1618*b* of the drive housing 1614. Each end 2802*a,b* of the lead screw 1622 is axially supported at the first and second ends 1618*a,b*, respectively to help prevent (minimize) linear movement of the lead screw 1622, while simultaneously allowing unrestricted rotational movement.

Referring to FIG. 28A, a driven gear 2804 is provided at or otherwise forms part of the distal end 2802*a* of the lead screw 1622. The driven gear 2804 is arranged to intermesh with a drive gear 2806 rotatably mounted at the first end 1618*a* of the drive housing 1614. The drive gear 2806 may form part of or may otherwise be operatively coupled to the first drive input 1636*a* (FIGS. 16 and 17B) such that rotation of the first drive input 1636*a* (via the first drive output 1724*a* of the instrument driver 1702 of FIGS. 17A-17B) correspondingly rotates the driven gear 2804, which causes rotation of the lead screw 1622. In other embodiments, the driven gear 2804 may be driven by a combination of the first drive input 1636*a* and at least one additional drive input (not shown). Using an additional drive input may be required if the torsional forces are high and can be distributed between two inputs. In at least one embodiment, the first drive input 1636*a* may comprise a direct input into the lead screw 1622 versus an arranged intermeshing of gears.

Referring to FIG. 28B, the proximal end 2802*b* of the lead screw 1622 may be rotatably mounted to the second end 1618*a* of the drive housing 1614. In some embodiments, one or more thrust bearings 2808 may be arranged at the proximal end 2802*b* of the lead screw 1622 to reduce rotational friction of the lead screw 1622 as it rotates.

Modular Separate Closure & Firing Style on Carriage Architecture

Figure 29:
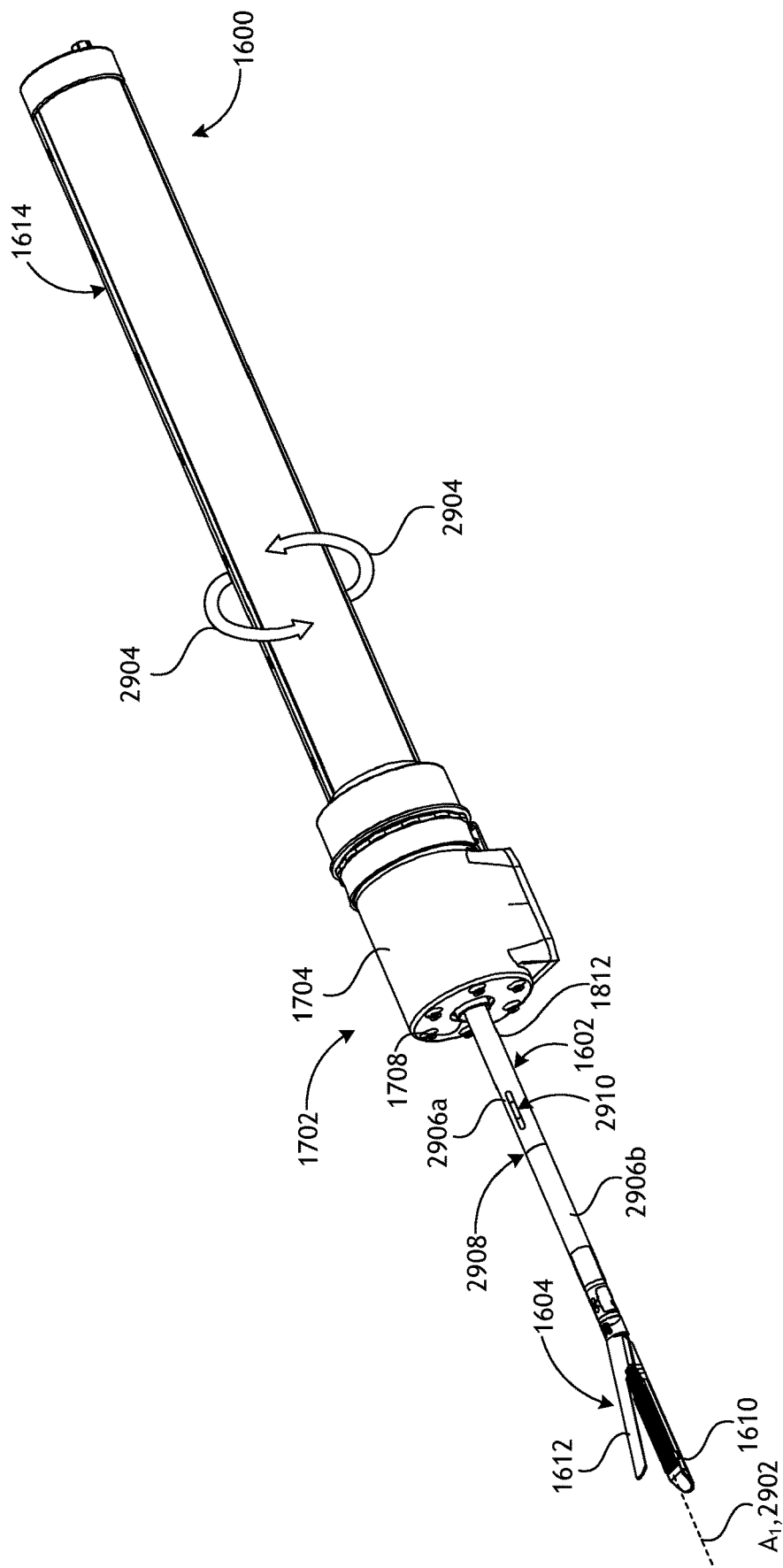
FIG. 29 is an isometric view of the surgical tool of FIG. 16 releasably coupled to the instrument driver of FIGS. 17A-17B, according to one or more embodiments.

FIG. 29 is an isometric view of the surgical tool 1600 of FIG. 16 releasably coupled to the instrument driver 1702 of FIGS. 17A-17B, according to one or more embodiments. As briefly discussed above, the instrument driver 1702 is configured to attach a surgical tool (i.e., the surgical tool 1600) to a surgical robotic arm, such as any of the robotic arms 104, 406 described herein. The end effector 1604 and the shaft 1602 can penetrate the instrument driver 1702 by extending through the central aperture 1708 defined longitudinally through the body 1704 of the instrument driver 1702.

In some embodiments, the instrument driver 1702 includes a tool drive assembly (not shown) capable of rotating independent of the body 1704 about a rotational axis 2902. When the surgical tool 1600 is mounted to the instrument driver 1702, the longitudinal axis $A_1$ of the surgical tool 1600 coaxially aligns with the rotational axis 2902 of the tool drive assembly such that actuating the tool drive assembly correspondingly causes the entire surgical tool 1600 to rotate or "roll" about the longitudinal axis $A_1$, as indicated by the arrows 2094. Consequently, actuation of the tool drive assembly allows the shaft 1602, the end effector 1604, and the drive housing 1614 to continuously roll about the longitudinal axis $A_1$ in either angular direction (i.e., clockwise or counter-clockwise) relative to the instrument driver 1702, which remain stationary. In contrast to other surgical tools where the shaft and the end effector are rotated independent of and relative to the remaining portions of the surgical tool, the shaft 1602, the end effector 1604, and the drive housing 1614 are each fixed in rotation, which enables the entire surgical tool 1600 to rotate as a single, monolithic unit.

According to one or more embodiments of the disclosure, the shaft 1602 may be modular and otherwise segmented into at least two portions or sections that are releasably coupled. More specifically, the shaft 1602 may comprise a first or "proximal" shaft portion 2906*a* releasably coupled to a second or "distal" shaft portion 2906*b*. The proximal shaft portion 2906*a* extends distally from the carriage 1626 (FIG. 16), and the distal shaft portion 2906*b* extends proximally from the end effector 1604. The proximal and distal shaft portions 2906*a,b* may be releasably coupled at a releasable interface 2908 located at some point along the shaft 1602 between the end effector 1604 and the carriage 1626. In some embodiments, the releasable interface 2908 may include a latch mechanism 2910 that may be manually manipulated by a user (e.g., a doctor, a nurse, an operator, etc.) to help facilitate the process of separating the distal shaft portion 2906*b* from the proximal shaft portion 2906*a*.

The releasable interface 2908 is configured to operatively and releasably couple proximal and distal portions of one or more features or mechanisms of the surgical tool 1600 that extend from the carriage 1626 (FIG. 16) to the end effector 1604 and cause the end effector 1604 to operate or articulate. In some embodiments, for example, the releasable interface 2908 may operatively and releasably couple proximal and distal portions of the closure tube 1812 such that actuation of the first activating mechanism 1638*a* (FIGS. 24A-25) will correspondingly open or close the jaws 1610, 1612 at the end effector 1604, as generally described above. In other embodiments, or in addition thereto, the releasable interface 2908 may operatively and releasably couple proximal and distal portions of the inner grounding shaft 1810 (FIGS. 18B-18C) and the first and second drive members 1816*a,b* (FIGS. 18C and 19) such that actuation of the second activating mechanism 1638*b* (FIGS. 18A-29) will correspondingly articulate the end effector 1604, as also generally described above. In yet other embodiments, or in addition to the foregoing, the releasable interface 2908 may operatively and releasably couple proximal and distal portions of the firing rod 2106 (FIGS. 21-22) such that actuation of the third activating mechanism 1638*c* (FIGS. 20-23) will correspondingly cause the knife 2302 (FIG. 23) to "fire", i.e., advance or retract, as also generally described above.

The releasable interface 2908 may prove advantageous in converting the end effector 1604, or any other type of end effector, into a disposable or consumable component part of the surgical tool 1600. More specifically, the releasable interface 2908 allows distal portions of the surgical tool 1600, including the end effector 1604, to be removed and replaced with a new or refurbished end effector. This may be beneficial, for instance, in allowing operators to easily and quickly replace the consumable knife 2302 (FIG. 23) and associated staple cartridge of the end effector 1604. Moreover, the releasable interface 2908 may prove advantageous in allowing the operator to easily and quickly replace the end effector 1604 with an end effector having a different length (e.g., 45 mm or 60 mm), or an end effector with differently designed jaws (e.g., jaws designed to go under a vessel with a curved tip or other shape).

Figure 30A:
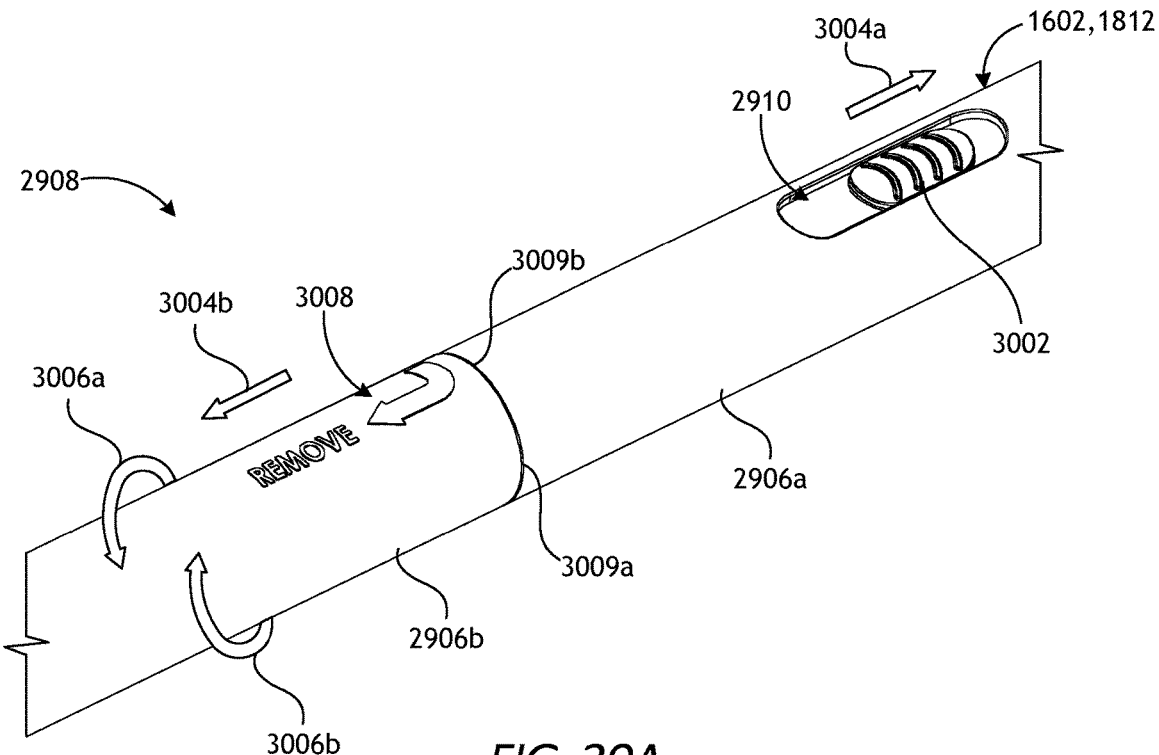
FIGS. 30A and 30B are isometric views of the releasable interface of FIG. 29 in coupled and released states, respectively, according to one or more embodiments.
Figure 30B:
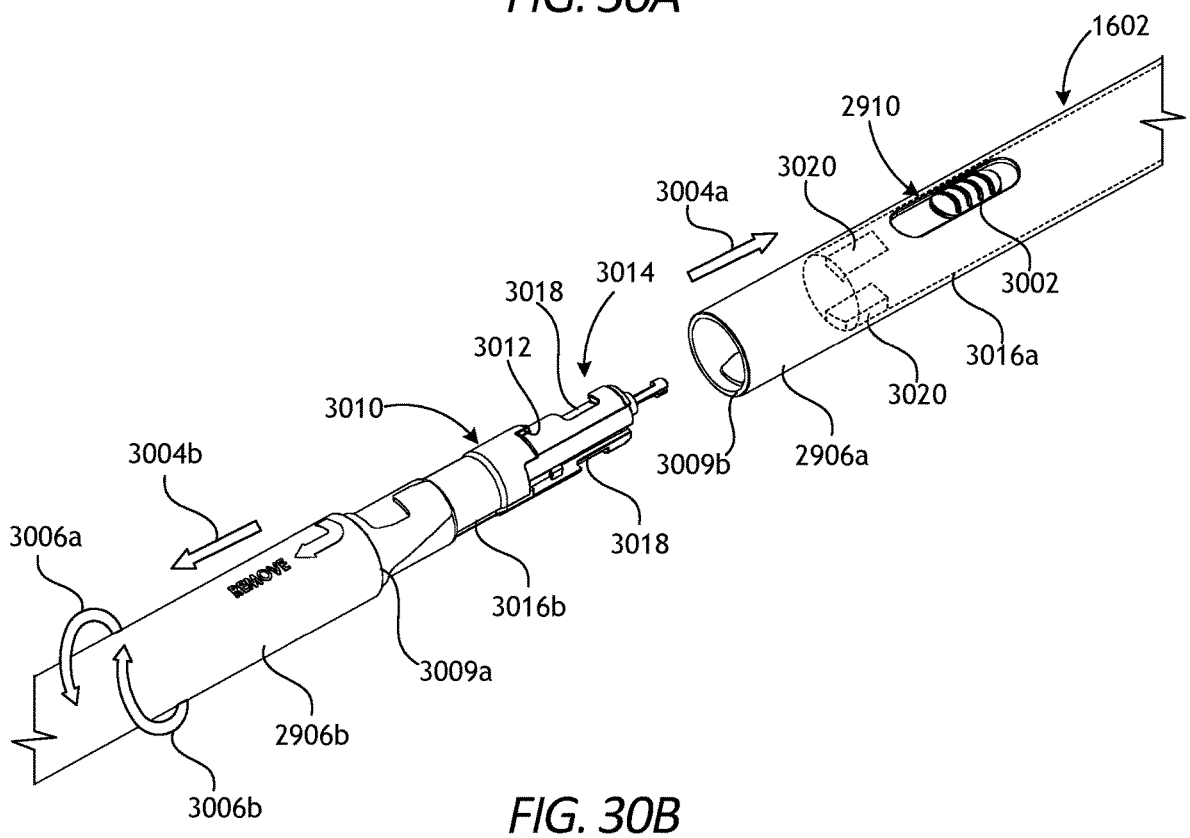

FIGS. 30A and 30B are isometric views of the releasable interface 2908 shown in coupled and released states, respectively, according to one or more embodiments. More specifically, FIG. 30A depicts the proximal and distal shaft portions 2906*a,b* of the shaft 1602 mated at the releasable interface 2908, and FIG. 30B depicts the proximal and distal shaft portions 2906a,b axially separated. The proximal and distal shaft portions 2906a,b may cooperatively form or otherwise provide the closure tube 1812, which, as described above, comprises the outer portion of the shaft 1602 and is movable (actuatable) to open or close the jaws 1610, 1612 (FIG. 29). Moreover, the proximal and distal shaft portions 2906a,b of the closure tube 1812 enclose the inner grounding shaft 1810 (FIGS. 18B-18C), the first and second drive members 1816a,b (FIGS. 18C and 19), and the firing rod 2106 (FIGS. 21-22).

Referring first to FIG. 30A, when it is desired to separate the distal shaft portion 2906b from the proximal shaft portion 2906a, and thereby remove the end effector 1604 (FIG. 29), the distal shaft portion 2906b may first be rotated in a first angular direction 3006a to disengage one or more internal couplings and subsequently advanced distally 3004b away from the proximal shaft portion 2906a. In some embodiments, when the latch mechanism 2910 is engaged, the proximal and distal shaft portions 2906a,b may be rotationally fixed and therefore unable to separate from one another. Consequently, the latch mechanism 2910 may help maintain the proximal and distal shaft portions 2906a,b coupled at the releasable interface 2908.

When it is desired to separate the distal shaft portion 2906b from the proximal shaft portion 2906a, the latch mechanism 2910 may be manually manipulated. More specifically, the latch mechanism 2910 may be manually manipulated by a user by engaging and manually moving a thumb pad 3002 proximally 3004a to disengage the latch mechanism 2910, which then allows the distal shaft portion 2906b to rotate relative to the proximal shaft portion 2906a in the first angular direction 3006a. Rotating the distal shaft portion 2906b in the first angular direction 3006a disengages the internal couplings of the releasable interface 2908, and once the internal couplings are disengaged, the user may move the distal shaft portion 2906b distally 3004b to separate the distal shaft portion 2906b from the proximal shaft portion 2906a, and simultaneously separate distal features or mechanisms of the surgical tool 1600 from proximal features or mechanisms of the surgical tool 1600. In one or more embodiments, one or more markings 3008 may be provided on the shaft 1602 (e.g., the distal shaft portion 2906b) indicating basic manual instructions on how to separate the distal shaft portion 2906b from the proximal shaft portion 2906a.

To reattach the distal shaft portion 2906b, or attach a new or refurbished distal shaft portion and corresponding end effector, the foregoing steps may be reversed. More specifically, the distal shaft portion 2906b may be moved proximally 3004a until a proximal end 3009a of the distal shaft portion 2906b engages (i.e., bottoms out) or comes into close contact with a distal end 3009b of the proximal shaft portion 2906b. Once the proximal and distal ends 3009a,b engage (or come into close contact), the distal shaft portion 2906b may be rotated in a second angular direction 3006b opposite the first angular direction 3006a and thereby re-engage the one or more internal couplings of the releasable interface 2908, which re-engage the distal features or mechanisms of the surgical tool 1600 to the proximal features or mechanisms of the surgical tool 1600. In some embodiments, the latch mechanism 2910 may be simultaneously manipulated by the user to allow the distal shaft portion 2906b to be rotated in the second angular direction 3006b. In other embodiments, however, the latch mechanism 2910 may be spring-loaded and otherwise able to snap into place as the distal shaft portion 2906b is rotated in the second angular direction 3006b.

It is noted that embodiments are contemplated herein where the latch mechanism 2910 is omitted from the releasable interface 2908 and may otherwise comprise an optional component of the releasable interface 2908. In such embodiments, the proximal and distal shaft portions 2906a,b may be rotationally held together using another type of device or mechanism, such as an interference fit, a dimple-protrusion interface, screw threads, a snap fit, a latching mechanism, or the like.

In FIG. 30B, the distal shaft portion 2906b has been moved distally 3004b, thereby exposing a proximal channel retainer 3010 of the releasable interface 2908. The proximal channel retainer 3010 may define or otherwise provide a latch interface notch 3012 engageable with a protrusion 3102 (FIG. 31) provided by the latch mechanism 2910. More specifically, the protrusion 3102 extends radially inward from the thumb pad 3002 and is engageable against the latch interface notch 3012 when the latch mechanism 2910 is engaged to prevent the distal shaft portion 2906b from rotating in the first angular direction 3006a relative to the proximal shaft portion 2906a. Once the latch mechanism 2910 is disengaged, and the protrusion 3102 disengages from the latch interface notch 3012, the distal shaft portion 2906b may then be free to rotate relative to the proximal shaft portion 2906a.

The proximal channel retainer 3010 may provide or support one or more internal couplings of the releasable interface 2908 that allow distal features or mechanisms of the surgical tool 1600 (FIG. 29) to be releasably coupled to corresponding proximal features or mechanisms of the surgical tool 1600. More specifically, and as described in more detail below, the proximal channel retainer 3010 may provide or support an internal coupling that allows the distal shaft portion 2906b to be releasably coupled to the proximal shaft portion 2906a, and further provides or supports various internal couplings that allow distal portions of the inner grounding shaft 1810 (FIGS. 18B-18C), the first and second drive members 1816a,b (FIGS. 18C and 19), and the firing rod 2106 (FIGS. 21-22) to be releasably coupled to corresponding proximal portions of the same.

In the illustrated embodiment, for example, the proximal channel retainer 3010 may provide or define an inner grounding shaft coupling 3014 used to releasably couple proximal and distal portions of the inner grounding shaft 1810 (FIGS. 18B-18C). More particularly, the inner grounding shaft coupling 3014 may be configured to releasably connect a proximal portion 3016a (shown in dashed lines) of the inner grounding shaft 1810, referred to herein as "the proximal inner grounding shaft 3016a", to a distal portion 3016b of the inner grounding shaft 1810, referred to herein as "the distal inner grounding shaft 3016b". As illustrated, the proximal and distal inner grounding shafts 3016a,b each extend within the proximal and distal shaft portions 2906a,b, respectively. The proximal inner grounding shaft 3016a extends from the carriage 1626 (FIG. 16), and the distal inner grounding shaft 3016b extends from the wrist 1606 (FIGS. 16, 19, and 25). In some embodiments, the proximal channel retainer 3010 may form part of or otherwise extend from the distal inner grounding shaft 3016b.

The inner grounding shaft coupling 3014 may comprise one or more pockets 3018 (two shown) defined on the distal inner grounding shaft 3016b configured to receive and axially retain a corresponding one or more projections 3020 (two shown in dashed lines) provided by or otherwise defined on the proximal inner grounding shaft 3016a. The projections 3020 may be received within the pockets 3018 by advancing the proximal channel retainer 3010 into the interior of the proximal shaft portion 2906a until the proximal end 3009a of the proximal shaft portion 2906a engages (or comes into close contact with) the distal end 3009b of the proximal shaft portion 2906b. The distal shaft portion 2906a may then be rotated in the second angular direction 3006b, which causes the projections 3020 to be received within the pockets 3018.

Figure 31:
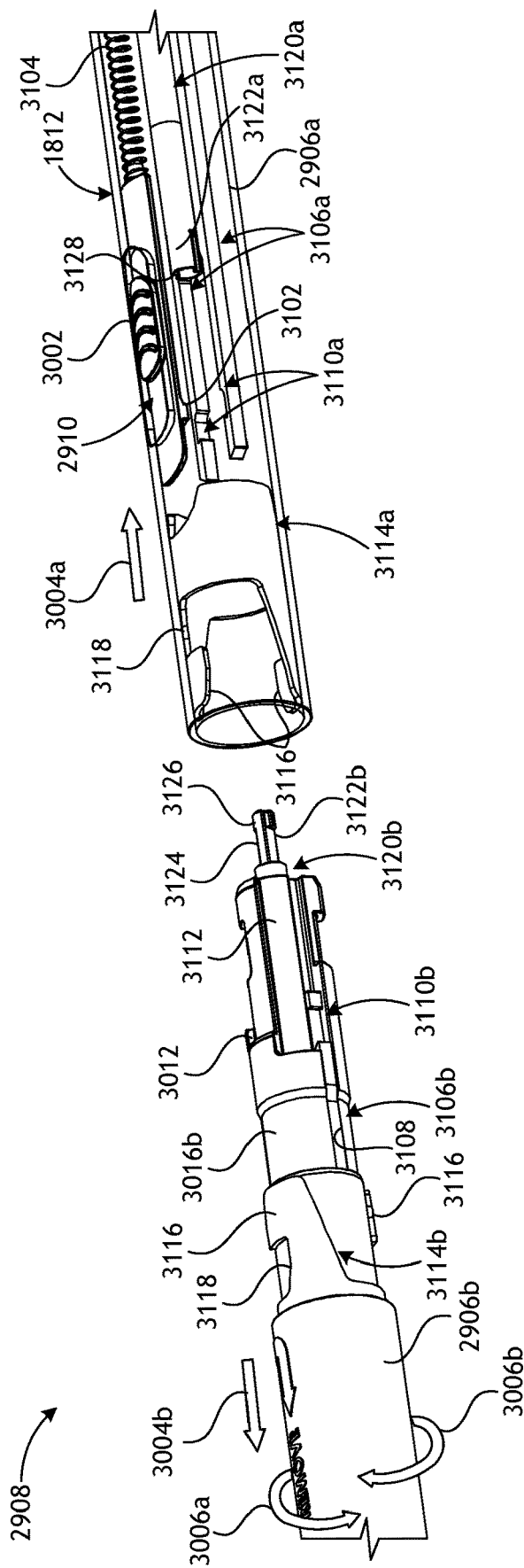
FIG. 31 is an enlarged isometric view of the releasable interface of FIGS. 29 and 30A-30B in the released state, according to one or more embodiments.

FIG. 31 is an enlarged isometric view of the releasable interface 2908 in the released state, according to one or more embodiments. In FIG. 31, the proximal shaft portion 2906a is shown in phantom and the proximal inner grounding shaft 3016a (FIG. 30B) is omitted to enable viewing of the various internal components of the releasable interface 2908.

As described above, the latch mechanism 2910 may provide a protrusion 3102 extending inward from the thumb pad 3002 and engageable with the latch interface notch 3012 of the proximal channel retainer 3010 to prevent the distal shaft portion 2906b from rotating in the first angular direction 3006a relative to the proximal shaft portion 2906a. Once the protrusion 3102 is disengaged from the latch interface notch 3012 by manually moving the latch mechanism 2910 proximally 3004a, the distal shaft portion 2906b may then be free to rotate relative to the proximal shaft portion 2906a, as described above. In some embodiments, as illustrated, the latch mechanism 2910 may be spring-biased and otherwise include a biasing member 3104 (e.g., a coil spring) that urges the latch mechanism 2910 distally 3004b. Consequently, when the user releases the thumb pad 3002 after moving the latch mechanism proximally 3004a, the biasing member 3104 will urge the thumb pad 3002 back to its initial location. This feature allows the latch mechanism 2910 to naturally remain engaged and thereby rotationally secure the distal and proximal shaft portions 2906a,b until the user manually disengages the latch mechanism 2910.

The proximal channel retainer 3010 may also provide or define a drive member coupling used to releasably couple proximal and distal portions of the first and second drive members 1816a,b (FIGS. 18C and 19). More particularly, the drive member coupling may be configured to releasably connect proximal portions 3106a of the drive members 1816a,b, referred to herein as "proximal drive member portions 3106a", to distal portions 3106b of the drive members 1816a,b, referred to herein as "distal drive member portions 3106a" (only one distal drive member portion 3106a visible in FIG. 31). As illustrated, the proximal and distal drive member portions 3106a,b extend within the proximal and distal shaft portions 2906a,b, respectively. The proximal drive member portions 3106a extend from the carriage 1626 (FIG. 16), and the distal drive member portions 3106b extend from the wrist 1606 (FIGS. 16, 19, and 25). Moreover, the proximal drive member portions 3106a may be arranged within corresponding slots (not shown) defined in the proximal inner grounding shaft 3016a (FIG. 30B), and the distal drive member portions 3106b may be arranged within corresponding slots 3108 (only one visible in FIG. 31) defined in the distal inner grounding shaft 3016b. The slots 3108 of the proximal and distal inner grounding shafts 3016a,b may be aligned with and otherwise contiguous with the slots 1818, 1820 (FIG. 18C) defined in the inner grounding shaft 1810 (FIGS. 18B-18C), and thus configured to guide the proximal and distal drive member portions 3106a,b as they axially translate.

The proximal drive member portions 3106a may provide or otherwise define first matable features 3110a configured to locate and mate with second matable features 3110b (only one visible in FIG. 31) provided or otherwise defined on the distal drive member portions 3106b. The matable features 3110a,b may comprise any matable device or mechanism that allows axial loads to be transmitted between the proximal and distal drive member portions 3106a,b when properly coupled. In the illustrated embodiment, for example, the matable features 3110a,b comprise matable castellations or notches. In other embodiments, the matable features 3110a,b may alternatively comprise circular expanding collets or press fit rings, without departing from the scope of the disclosure.

The matable features 3110a,b may be mated by advancing the proximal channel retainer 3010 into the interior of the proximal shaft portion 2906a until the proximal end 3009a of the proximal shaft portion 2906a engages (or comes into close contact with) the distal end 3009b of the proximal shaft portion 2906b. As the proximal channel retainer 3010 is advanced into the proximal shaft portion 2906a, the proximal drive member portions 3106a may traverse corresponding channels 3112 (only one visible in FIG. 31) defined on the proximal channel retainer 3010 and angularly offset from the slots 3108 defined in the distal inner grounding shaft 3016b. Once the proximal end 3009a of the proximal shaft portion 2906a engages (or comes into close contact with) the distal end 3009b of the proximal shaft portion 2906b, the distal shaft portion 2906a may then be rotated in the second angular direction 3006b, which causes the second matable features 3110b to be received by or otherwise interlock with the corresponding first matable features 3110a. With the first and second matable features 3110a,b properly mated or interlocked, the second activating mechanism 1638b (FIGS. 18A-29) may be actuated to move the first and second drive members 1816a,b (FIGS. 18C and 19), which correspondingly moves the interlocked proximal and distal drive member portions 3106a,b, and thereby articulates the end effector 1604, as generally described above.

The proximal channel retainer 3010 may also provide or define a closure tube coupling used to releasably couple the proximal and distal shaft portions 2906a,b of the closure tube 1812, which, as described above, is movable (actuatable) to open or close the jaws 1610, 1612 (FIG. 29). The closure tube coupling may include or otherwise provide a first or "proximal" tube coupling 3114a and a second or "distal" tube coupling 3114b. The proximal tube coupling 3114a may be provided on the proximal shaft portion 2906a and configured to locate and mate with the distal tube coupling 3114b provided on the distal shaft portion 2906b. In some embodiments, the proximal and distal tube couplings 3114a,b may be defined by the proximal and distal shaft portions 2906a,b, respectively, and may thus form integral parts thereof. In other embodiments, however, one or both of the proximal and distal tube couplings 3114a,b may comprise separate component parts mounted or otherwise secured to the proximal and distal shaft portions 2906a,b, respectively. In either embodiment, axial movement of the proximal and distal shaft portions 2906a,b will correspondingly move the proximal and distal tube couplings 3114a,b.

In the illustrated embodiment, the proximal and distal tube couplings 3114a,b comprise separate component parts mounted to the interior of the proximal and distal shaft portions 2906a,b, respectively, and otherwise interposing the proximal and distal shaft portions 2906a,b and the proximal and distal inner grounding shafts 3016a and 3016b (FIG. 30B), respectively. The proximal and distal tube couplings 3114a,b may comprise any type of device or mechanism that facilitates axial load transmission between the proximal and distal shaft portions 2906a,b when properly coupled. In the illustrated embodiment, for example, the proximal and distal tube couplings 3114a,b comprise matable bayonet-style couplings including one or more tabs 3116 matable with one or more corresponding cutouts 3118. In other embodiments, the proximal and distal tube couplings 3114a,b may alternatively comprise expanding collets, rings, press fits, or clamp-type ball connections, without departing from the scope of the disclosure.

The proximal and distal tube couplings 3114a,b may be mated by advancing the proximal channel retainer 3010 into the interior of the proximal shaft portion 2906a until the proximal end 3009a of the proximal shaft portion 2906a engages (or comes into close contact with) the distal end 3009b of the proximal shaft portion 2906b. Once the proximal and distal ends 3009a,b engage (or come into close contact), the distal shaft portion 2906a may then be rotated in the second angular direction 3006b, which causes the tabs 3116 of each tube coupling 3114a,b to be received into or otherwise interlock with the corresponding cutouts 3118 of the opposing tube coupling 3114a,b. With the first and second proximal and distal tube couplings 3114a,b properly mated or interlocked, the first activating mechanism 1638a (FIGS. 24A-25) may be actuated to move the closure tube 1812 and correspondingly open or close the jaws 1610, 1612 (FIG. 29) at the end effector 1604 (FIG. 29), as generally described above.

The proximal channel retainer 3010 may also provide or define a firing rod coupling used to releasably couple proximal and distal portions of the firing rod 2106 (FIGS. 21-22). More particularly, the firing rod coupling may be configured to releasably connect a proximal firing rod portion 3120a to a distal firing rod portion 3120b. The proximal and distal firing rod portions 3120a,b are aligned with and otherwise form contiguous (but separable) portions of the firing rod 2106. The proximal firing rod portion 3120a extends from the carriage 1626 (FIG. 16) within the proximal inner grounding shaft 3016a (FIG. 30B), and the distal firing rod portion 3120b extends from the wrist 1606 (FIGS. 16, 19, and 25) within the distal inner grounding shaft 3016b. The proximal and distal firing rod portions 3120a,b may each be axially translatable relative to the proximal and distal inner grounding shafts 3016a,b, respectively, thus allowing the firing rod 2106 to advance or retract the knife 2302 (FIG. 23), as generally described above.

The proximal firing rod portion 3120a may provide or otherwise define a first matable feature 3122a configured to locate and mate with a second matable feature 3122b provided or otherwise defined on the distal firing rod portion 3120b. The matable features 3122a,b may comprise any matable device or mechanism that allows axial loads to be transmitted between the proximal and distal firing rod portions 3120a,b when properly coupled. In the illustrated embodiment, for example, the second matable feature 3122b comprises an axial extension 3124 terminating with a geometric fitting 3126, and the first matable feature 3122a comprises a tubular receptacle 3128 configured to receive the axial extension 3124 and the geometric fitting 3126. Mating the geometric fitting 3126 with the tubular receptacle 3128 may facilitate push and pull engagement through rotationally engaged notches. In other embodiments, however, the first and second matable features 3122a,b may comprise a threaded interface, without departing from the scope of the disclosure.

The matable features 3122a,b may be mated by advancing the proximal channel retainer 3010 into the interior of the proximal shaft portion 2906a until the proximal end 3009a of the proximal shaft portion 2906a engages (or comes into close contact with) the distal end 3009b of the proximal shaft portion 2906b. As the proximal channel retainer 3010 is advanced into the proximal shaft portion 2906a, the second matable feature 3122b of the distal firing rod portion 3120b may be received by or within the first matable feature 3122a of the proximal firing rod portion 3120a. Once the proximal and distal ends 3009a,b engage (or come into close contact), the distal shaft portion 2906a may then be rotated in the second angular direction 3006b, which correspondingly rotates the second matable feature 3122b within the first matable feature 3122a and thereby interlocks the matable features 3122a,b. With the first and second matable features 3122a,b properly mated or interlocked, the third activating mechanism 1638c (FIGS. 20-23) may be actuated to move the firing rod 2106 (FIGS. 21-22), which correspondingly causes the knife 2302 (FIG. 23) to "fire", i.e., advance or retract, as generally described above.

In some embodiments, as indicated above, movement of the firing rod 2106 (FIGS. 21-22) in the distal direction may also cause the jaws 1610, 1612 (FIG. 29) to close. In such embodiments, the proximal and distal shaft portions 2906a,b may remain stationary while the proximal and distal firing rod portions 3120a,b are axially advanced or retracted relative to the proximal and distal inner grounding shafts 3016a (FIG. 30B) and 3016b, and the knife 2302 (FIG. 23) is correspondingly advanced or retracted. Moreover, the firing rod 2106 (e.g., the distal firing rod portion 3120b) or the knife 2302 may include a feature or structure configured to engage and force the second jaw 1612 to close. As indicated above, this approach is commonly referred to as "knife-based" closure, and in such embodiments, the jaws 1610, 1612 may be spring biased to the open position when the knife 2302 is fully retracted. Alternatively, if the jaws 1610, 1612 are not spring biased to the open position, the knife 2302 could engage a separate opening member to move the jaws 1610, 1612 back to the open position while retracting the knife 2302.

4. Implementing Systems and Terminology

The specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
a drive housing having a lead screw extending from a first end of the drive housing;
a carriage movably mounted to the lead screw at a carriage nut secured to the carriage;
an elongate shaft extending from the carriage and penetrating the first end, the shaft having an end effector arranged at a distal end thereof and comprising a proximal shaft portion releasably coupled to a distal shaft portion at a releasable interface; and
proximal and distal portions of one or more mechanisms of the surgical tool extending from the carriage to the end effector within the proximal and distal shaft portions, respectively,
wherein the one or more mechanisms are operable to operate or articulate the end effector, and wherein the proximal and distal portions are releasably coupled at the releasable interface.

2. The robotic surgical tool of claim 1, further comprising:
a drive input arranged at the first end and operatively coupled to the lead screw such that rotation of the drive input correspondingly rotates the lead screw; and
an instrument driver arranged at an end of a robotic arm and matable with the drive housing at the first end, the instrument driver providing a drive output matable with the drive input such that rotation of the drive output correspondingly rotates the drive input and thereby rotates the lead screw,
wherein rotation of the lead screw moves the carriage and the carriage nut axially along the lead screw and thereby moves the one or more mechanisms and the end effector distally or proximally.

3. The robotic surgical tool of claim 2, wherein the shaft penetrates the instrument driver by extending through a central aperture defined longitudinally through the instrument driver.

4. The robotic surgical tool of claim 1, further comprising a latch mechanism that rotationally fixes the distal shaft portion to the proximal shaft portion when engaged and thereby prevents the proximal and distal shaft portions from separating.

5. The robotic surgical tool of claim 1, further comprising an activating mechanism mounted to the carriage and actuatable to advance or retract the proximal and distal shaft portions relative to the one or more mechanisms and thereby close or open jaws of the end effector.

6. The robotic surgical tool of claim 1, wherein the releasable interface includes:
a proximal channel retainer at least partially receivable within the proximal shaft portion; and
one or more internal couplings supported by the proximal channel retainer, each internal coupling releasably coupling the proximal and distal portions of a corresponding one of the one or more mechanisms.

7. The robotic surgical tool of claim 6, wherein the one or more internal couplings comprises an inner grounding shaft coupling comprising:
a proximal inner grounding shaft extending within the proximal shaft portion from the carriage;
a distal inner grounding shaft extending within the distal shaft portion from the end effector;
one or more projections provided by the proximal inner grounding shaft; and
one or more pockets defined on the distal inner grounding shaft and configured to receive and axially retain the one or more projections and thereby couple the proximal and distal inner grounding shafts.

8. The robotic surgical tool of claim 7, wherein the one or more internal couplings further comprises a drive member coupling comprising:
proximal drive member portions corresponding to first and second drive members extending from the carriage and extending within corresponding slots defined in the proximal inner grounding shaft;
distal drive member portions corresponding to the first and second drive members extending from the end effector and extending within corresponding slots defined in the distal inner grounding shaft;
first matable features provided on the proximal drive member portions; and
second matable features provided on the distal drive member portions and matable with the first matable features to interconnect the proximal and distal drive members, wherein actuation of the first and second drive members moves the proximal and distal drive member portions and thereby articulates the end effector.

9. The robotic surgical tool of claim 6, wherein the one or more internal couplings comprises a closure tube coupling that releasably couples the proximal and distal shaft portions, the closure tube coupling comprising:
a proximal tube coupling secured to the proximal shaft portion; and
a distal tube coupling secured to the distal shaft portion and matable with the proximal tube coupling.

10. The robotic surgical tool of claim 9, wherein the proximal and distal tube couplings comprise matable bayonet-style couplings.

11. The robotic surgical tool of claim 6, wherein the one or more internal couplings comprises a firing rod coupling comprising:
a proximal firing rod portion corresponding to a firing rod extending from the carriage and providing a first matable feature; and
a distal firing rod portion corresponding to the firing rod extending from the end effector and providing a second matable feature matable with the first matable feature to interconnect the proximal and distal firing rod portions,
wherein actuation of the firing rod causes the proximal and distal firing rod portions to advance or retract and simultaneously advance or retract a knife at the end effector.

12. The robotic surgical tool of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

13. A robotic surgical tool, comprising:
a drive housing having a lead screw extending from a first end of the drive housing;
a carriage movably mounted to the lead screw at a carriage nut secured to the carriage;
an elongate shaft extending from the carriage and penetrating the first end, the shaft having an end effector arranged at a distal end thereof and comprising a proximal shaft portion releasably coupled to a distal shaft portion at a releasable interface; and
a firing rod extending from the carriage and operatively coupled to a knife at the end effector, the firing rod comprising a proximal firing rod portion releasably coupled to a distal firing rod portion at the releasable interface,
wherein longitudinal movement of the firing rod correspondingly moves the knife in the same direction relative to the proximal and distal shaft portions and simultaneously closes or opens jaws of the end effector.

14. The robotic surgical tool of claim 13, further comprising:
a first matable feature provided on the proximal firing rod portion; and
a second matable feature provided on the distal firing rod portion and matable with the first matable feature to interconnect the proximal and distal firing rod portions.

* * * * *